(12) United States Patent
Takeuchi et al.

(10) Patent No.: US 6,239,534 B1
(45) Date of Patent: May 29, 2001

(54) PIEZOELECTRIC/ELECTROSTRICTIVE DEVICE

(75) Inventors: Yukihisa Takeuchi, Nishikamo-gun; Takao Ohnishi, Nishikasugai-gun; Koji Kimura, Nagoya, all of (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 09/242,642

(22) Filed: Dec. 28, 1998

(30) Foreign Application Priority Data

Sep. 4, 1998 (WO) .................................. PCT/JP98/03971

(51) Int. Cl.$^7$ .................................................. H01L 41/08
(52) U.S. Cl. ............................................................. 310/328
(58) Field of Search .................................. 310/328, 331, 310/324

(56) References Cited

U.S. PATENT DOCUMENTS

| | | | |
|---|---|---|---|
| 5,410,207 | * | 4/1995 | Miura et al. ........................... 310/328 |
| 5,489,812 | * | 2/1996 | Furuhata et al. ................... 310/328 X |
| 5,867,302 | * | 2/1999 | Fleming ............................ 310/328 X |
| 5,917,271 | * | 6/1999 | Yamamura ........................... 310/328 |
| 5,942,837 | * | 8/1999 | Reuter ................................ 310/328 |

FOREIGN PATENT DOCUMENTS

| | | |
|---|---|---|
| 61-46082 | 3/1986 | (JP) . |
| 61-185982 | 8/1986 | (JP) . |
| 62-201956 | 12/1987 | (JP) . |
| 63-64640 | 3/1988 | (JP) . |
| 63-224275 | 9/1988 | (JP) . |
| 64-351 | 1/1989 | (JP) . |
| 64-35767 | 3/1989 | (JP) . |
| 3-34259 | 4/1991 | (JP) . |
| 4-62984 | 2/1992 | (JP) . |
| 6-104503 | 4/1994 | (JP) . |
| 6-164007 | 6/1994 | (JP) . |
| 10-136665 | 5/1998 | (JP) . |

OTHER PUBLICATIONS

Nakamura, S., et al., "An Electrostatic Micro Actuator for a Magnetic Head Tracking System of Hard Disk Drives," 1997 International Conference on Solid–State Sensors and Actuators, Chicago, Jun. 16–19, 1997, pp. 1081–1084.

Uchino, Kenji, "Form Foundation up to Application Piezo-electric/Electrostrictive Actuator," Japan Industrial Technique Center, Morikita Shuppan, pp. 161–162.

Koganezawa, S., et al., "Shear Mode Piezoelectric Micro-actuator for Magnetic Disk Drives," IEEE Transactions on Magnetics, vol. 34, No. 4, Jul. 1998, pp. 1910–1912.

* cited by examiner

*Primary Examiner*—Mark O. Budd
(74) *Attorney, Agent, or Firm*—Burr & Brown

(57) ABSTRACT

A piezoelectric/electrostrictive device is provided in which a connection plate whose one end in the longitudinal direction is held by two diaphragms and whose other end is held by two other diaphragms is spanned between bottoms of faced concave portions formed on a substrate, and piezoelectric elements are arranged on at least a part of at least one-side plane surface of each of the diaphragms, and the diaphragms are connected with the sides of the concave portions in at least the direction for the diaphragms to hold the connection plate, and a fixing plate is connected to the connection plate so that the longitudinal direction of the fixing plate becomes parallel with the direction for the diaphragms to hold the connection plate. A displacement of the fixing plate generated by applying a voltage to the piezoelectric element is utilized or an electromotive force of the piezoelectric element based on a displacement of the fixing plate is utilized. The piezoelectric/electrostrictive device is preferably used as a positioning- or angle-adjustment mechanism of an optical unit or precision unit, a vibrator or resonator for communication or motive power, an oscillator, a discriminator, an ultrasonic sensor, or an acceleration sensor because the device is able to convert electric energy into mechanical energy such as a mechanical displacement, force, or vibration and vice versa.

45 Claims, 11 Drawing Sheets

(a)   (b)

(a)

(b)

(c)

(a)

(b)

(c)

(d)

(a)

(b)

(c)

(d)

PIEZOELECTRIC/ELECTROSTRICTIVE DEVICE

BACKGROUND OF THE INVENTION AND RELATED ART STATEMENT

The present invention relates to a device using a piezoelectric/electrostrictive film, particularly to the structure of a piezoelectric/electrostrictive device for improving the operational characteristic of an element for converting electrical energy into mechanical energy such as mechanical displacement, mechanical force, or vibration and vice versa. Specifically, the present invention relates to a piezoelectric/electrostrictive device to be applied to each transducer, various actuators, frequency-region functional components (filters), transformers, vibrators and resonators for communication and motive power, oscillators, discriminators, and various sensors including ultrasonic sensors, acceleration sensors, angular velocity sensors, impact sensors, and mass sensors, and moreover unimorph- and bimorph-type elements used for servo shift elements described in "From foundation up to application of piezoelectric/electrostrictive actuator" written by Kenji Uchino {edited by Japan Industrial Technique Center and published by MORIKITA SHUPPAN (transliterated)}, and to be preferably adopted to various actuators used for mechanisms for shift and positioning adjustment and angle adjustment of various precision components and, optical equipment and precision equipment.

Recently, a shift control element for adjusting an optical-path length or position on the sub-micron order has been requested in optical and magnetic recording fields and the precision-machining field. To respond to this request, development of a piezoelectric/electrostrictive actuator or the like is progressed which is an element using a displacement based on the reverse piezoelectric effect or electrostrictive effect caused by applying an electric field to a piezoelectric/electrostrictive material such as a ferroelectric.

In the magnetic recording field which uses hard disc drives, storage capacity has been remarkably increased in recent years. This is because the a recording medium is used more efficiently by increasing the number of recording tracks to increase the recording density in addition to improvements in of recording methods.

This attempt has been mainly made so far on the improvement of a voice coil motor. Moreover, as a new technical art, an attempt has been made to apply an electrostatic-type microactuator fabricated by the micromachine process of Si or Ni to the tracking system of a hard-disk magnetic head is described on pp. 1081–1084 in the preliminary manuscript collection of "1997 International Conference on solid-state Sensors and Actuators" of "TRANSDUCER' 97".

Moreover, Japanese Patent Application Laid-Open No. 10-136665 discloses a piezoelectric actuator as shown in FIG. 16 in which a fixed portion 103, a movable portion 104, and at least one beam portion 102 for connecting the portions 103 and 104 to each other are integrally formed by forming at least one hole on a flat body made of a piezoelectric/electrostrictive material, and a strain generation portion is constituted by forming an electrode layer 105 on at least a part of at least one beam portion 102 so that an expansion or a contraction motion occurs in the direction connecting the fixed portion 103 with the movable portion 104, and a displacement mode of the movable portion 104 to the fixed portion 103 generated due to the expansion or contraction motion of the strain generation portion is an arc-shaped or rotational mode in the plane of the flat body.

However, in the case of the conventional art for positioning a recording head mainly using a voice coil motor, it is difficult to accurately position a recording head so as to accurately trace tracks when the number of tracks increases in order to correspond to further increase in capacity.

The above-described technical art using an electrostatic-type microactuator obtains a displacement by applying a voltage between a plurality of flat electrodes formed through micromachining. However, it is difficult to raise a resonance frequency because of the structure. Consequently, the technical art includes such problems that vibrations are not easily attenuated when a high-speed operation is performed and the positioning accuracy is deteriorated. Moreover, there is a feature that the technical art is displacement-theoretically inferior in the linearity of the voltage-displacement characteristic. Therefore, there are many problems to be solved from the viewpoint of accurate alignment. Furthermore, the process of micromachining itself has a problem from the viewpoint of manufacturing cost.

Furthermore, in the case of a piezoelectric actuator disclosed in Japanese Patent Application Laid-Open No. 10-136665, the piezoelectric-operation portion has a monomorph structure. Therefore, the main-strain axis of a piezoelectric film becomes coaxial or parallel with the main-shift axis of the piezoelectric-operation portion. Thus, there are problems that the piezoelectric-operation portion itself generates only a small shift and the movable portion also has a small displacement. Moreover, the piezoelectric actuator itself is heavy and subject to harmful vibrations for operation such as residual vibrations and vibrational noises under a high-speed operation as described in Japanese Patent Application Laid-Open No. 10-136665 and therefore, it is necessary to suppress harmful vibrations by injecting a filler into a hole. However, the use of such a filler may exert a bad influence upon a displacement of the movable portion. Moreover, because it is unavoidable to constitute a piezoelectric actuator with a piezoelectric/electrostrictive material inferior in mechanical strength, there is a problem that the actuator is subject to restriction concerning material strength, which in turn inhibits choice of shape and.

SUMMARY OF THE INVENTION

The present invention is made to solve the problems of the above described piezoelectric/electrostrictive device and its object is to provide a piezoelectric/electrostrictive device capable of obtaining a large displacement due to in-plane motion or rotational motion quickly and precisely.

That is, the present invention provides a piezoelectric/electrostrictive device as a first piezoelectric/electrostrictive device, characterized in that a connection plate whose one end in the longitudinal direction is held by at least two diaphragms and whose other end is held by at least two other diaphragms, is spanned between bottoms of faced concave portions formed in a substrate, and a piezoelectric element is secured to at least a part of at least one plane surface of each diaphragm, and each diaphragm is connected with the side of each concave portion in the direction in which each diaphragm holds the connection plate, and a fixing plate is connected to the connection plate so that the longitudinal direction of the fixing plate becomes parallel with the direction in which the diaphragms hold the connection plate.

In the case of the first piezoelectric/electrostrictive device, it is preferable to form a notch at the joint between the fixing plate and the connection plate. Moreover, it is possible to divide the connection plate into two plates in the spanning direction of the connection plate to form a gap at the center of the connection plate and connect the fixed plate to the flat-plate surface of the connection plate so as to cross the gap. In this case, it is preferable to form the notch at an end of the fixing plate at the position crossing the divided connection plates. Moreover, a structure of connecting the fixed plate to the connection plate so as to intersect each other is preferably adopted.

Furthermore, it is also preferable to form the notch at the connection plate between the joint between the connection plate and the substrate and the joint between the connection plate and the diaphragms. Furthermore, it is possible to use a structure in which the connection plate is divided into at least two plates in the longitudinal direction of the fixing plate and connected to at least two connection plates formed by dividing the fixed plate. Furthermore, it is preferable to form a hinge portion on the fixing plate from the joint between the fixing plate and the connection plate toward the longitudinal direction of the fixing plate.

In the case of the first piezoelectric/electrostrictive device, an operating method is preferably adopted that drives a set of piezoelectric elements located at diagonal positions about the joint between the fixing plate and the connection plate at the same phase and drives another set of piezoelectric elements at the opposite phase. On the other hand, such an operating method is adopted that drives a set of piezoelectric elements located at line-symmetric positions at the same phase by using the longitudinal axis of the fixing plate as a symmetric axis and drives another set of piezoelectric elements at the opposite phase. By the way, in the case of a piezoelectric/electrostrictive device of the present invention, it is possible to use a structure in which a pair of diaphragms for holding a connection plate are respectively connected with a connection plate at positions shifted in the thickness direction of the connection plate. In this case, it is also possible to use an operating method of arranging a piezoelectric element on one plane surface of each diaphragm by using the middle point between the joint positions between two diaphragms holding the connection plate and the connection plate as a point-symmetric center and by driving these piezoelectric elements at the same phase.

The present invention provides a piezoelectric/electrostrictive device as a second piezoelectric/electrostrictive device, characterized in that a connection plate is spanned between the sides of concave portions formed on a substrate, at least two diaphragms in which piezoelectric elements are arranged on at least a part of at least one plane surface are spanned between the connection plate and the bottom of the concave portion of the substrate, and a fixing plate is connected to the connection plate so that the longitudinal direction of the fixing plate becomes parallel with the spanning direction of the diaphragms.

In the case of the second piezoelectric/electrostrictive device, a structure is also preferably adopted in which at least two pairs of diaphragms constituted so that their plane surfaces face each other are spanned between the connection plate and the bottom of the concave portion of the substrate. Moreover, it is preferable to form a notch at the joint between a fixing plate and a connection plate. Furthermore, it is possible to use a structure in which a connection plate is divided into two plates in the spanning direction of the connection plate to form a gap at the center of the connection plate and the fixing plate is connected to the flat-plate surface of the connection plate so as to cross the gap. It is preferable to form a notch at an end of the fixing plate at the position crossing the divided connection plate.

In the case of the first and second piezoelectric/electrostrictive devices of the present invention, it is preferable that every connection between two optional members selected from a connection plate, diaphragm, and substrate is made at each side. Therefore, except the case of dividing a connection plate in its spanning direction, it is preferable that a fixing plate is also connected with a connection plate at each side. Moreover, it is preferable that at least a connection plate, diaphragm, and substrate are integrally formed. Therefore, also in this case, except the case of dividing a connection plate in its spanning direction, it is preferable that a fixing plate is also formed integrally with a connection plate. The above side connection or integral structure of various portions can be easily obtained by fabricating various portions of a device such as at least a substrate, a fixing plate, connection plate, and diaphragm except a piezoelectric element through the green-sheet laminating method.

A piezoelectric/electrostrictive device of the present invention uses a displacement of a fixing plate, particularly a displacement of the front end of the fixing plate. As the displacement mode of the fixing plate, it is preferable to use at least any one of the axial mode in the longitudinal direction of the fixing plate, in-plane rotational mode about the vicinity of the joint between the fixing plate and a connection plate, or axial rotational mode about the longitudinal axis of the connection plate. For the rotational mode, it is preferable to use one based on a magnification mechanism for magnifying a displacement of a piezoelectric element in two steps. In this case, "the magnification mechanism for magnifying an object in two steps" represents a magnification mechanism for magnifying a displacement generated by a piezoelectric element up to a flexural or bending displacement of a connection plate and thereafter further magnifying the magnified displacement up to a displacement of the rotational mode of a fixing plate. These various displacement modes are carried out by controlling the arrangement position of a diaphragm and a piezoelectric element or the driving phase of the piezoelectric element. Moreover, it is also preferable to divide one piezoelectric element into two elements and use one element as a driving element and the other element as an auxiliary element. In this case, the auxiliary element represents a troubleshooting element, displacement confirmation/decision element, or driving-support element and the like.

It is preferable to coat a piezoelectric element and an electrode lead electrically connected with the piezoelectric element with an insulating coating material made of resin or glass. Fluorocarbon polymer or silicone resin is preferably used as the above resin. Thus, when forming the insulating coating layer, it is preferable to form a shielding layer made of a conductive member on the surface of the insulating coating layer.

Fully-Stabilized zirconia or partially-stabilized zirconia is preferably used as the material of a substrate, fixing plate, connection plate, and diaphragm. On the other hand, a material mainly containing a component made of lead zirconate, lead titanate, and lead magnesium niobate is preferably used as the piezoelectric film of a piezoelectric element. At least any one of the shapes of a fixing plate, connection plate, and diaphragm can be easily dimension-adjusted by trimming the shape through laser-beam processing or cutting. It is also preferable to adjust the available electrode area of a piezoelectric element by laser-beam-processing or cutting the electrode of a piezoelectric element. In the case of the present invention, it is also preferable to form the above-described two piezoelectric/electrostrictive devices or more into one piezoelectric/electrostrictive device by uniting the piezoelectric/electrostrictive devices so that the fixing plates of them are connected with each other.

As the result of comparing a piezoelectric/electrostrictive device of the present invention with the piezoelectric actuator disclosed in the official gazette of Japanese Patent Laid-Open No. 136665/1998 described above, because the piezoelectric/electrostrictive device of the present invention has a unimorph or bimorph structure having a diaphragm, it is found that the axis of main strain of the piezoelectric film is different from the main displacement axis of the piezoelectric-operation portion (portion causing a displacement due to the strain of the piezoelectric film) in direction and the strain of the piezoelectric film can be magnified into a bending mode by using this feature. Therefore, a piezoelectric/electrostrictive device of the present invention is characterized in that a large amount of displacement of fixing-plate can be obtained. Moreover, a piezoelectric/electrostrictive device of the present invention allows functional differentiation and its substrate and the like other than its piezoelectric film can be constituted with a material mainly containing zirconia superior in mechanical strength and toughness. Therefore, there is an advantage that a compact, thin, and lightweight device having a desired strength can be obtained. Furthermore, a piezoelectric/electrostrictive device of the present invention has such a feature that the displacing characteristic is not easily influenced from the outside and therefore, a filler or the like is unnecessary.

"Piezoelectric" of a piezoelectric element, piezoelectric film, and piezoelectric ceramics used for the present invention include the meanings of both "piezoelectric" and "electrostrictive."

BEST MODE OF CARRYING OUT THE INVENTION

Figure 1:
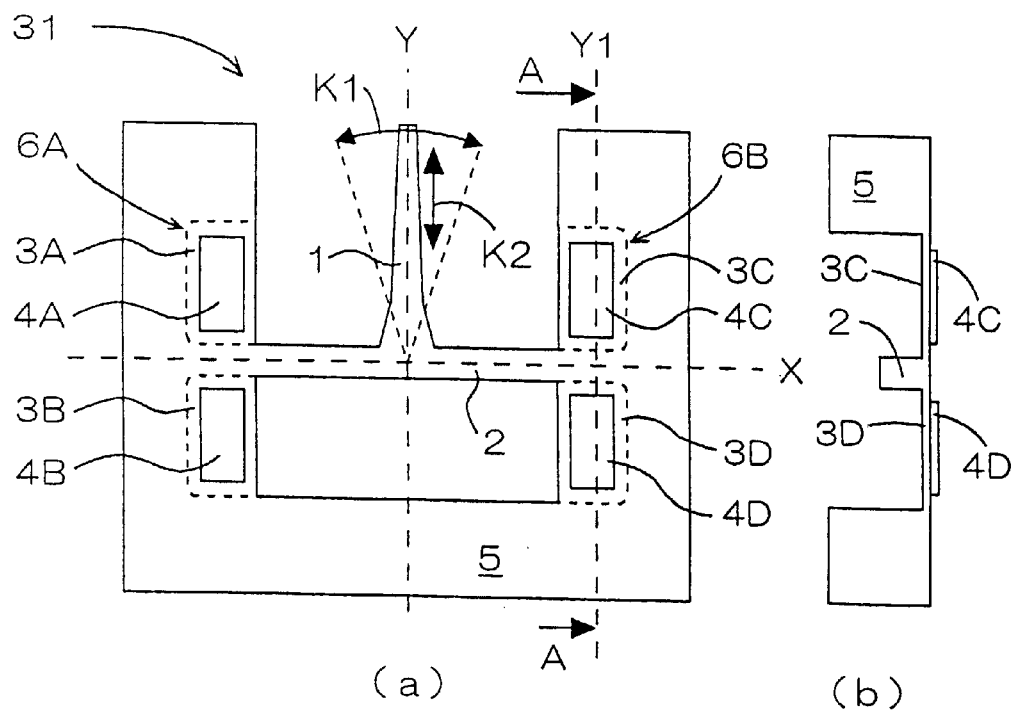
FIG. 1 shows a top view and a sectional view of an embodiment of a piezoelectric/electrostrictive device of the present invention.

FIG. 1(a) shows a top view of an embodiment of a first piezoelectric/electrostrictive device (hereafter referred to as "device") 31 and FIG. 1(b) shows a sectional view of a plane passing through Y1 axis and vertical to plane X-Y, that is, a sectional view of the cross section of the device 31 in plane Y-Z viewed from the X-axis direction (hereafter, the sectional view of FIG. 1(b) is expressed as "arrow AA view on Y1 axis"). In this case, while one end of a connection plate 2 of the device 31 in its longitudinal direction (X-axis direction) is held by two diaphragms 3A and 3B and the other end of the plate 2 is held by other two diaphragms 3C and 3D, these ends are spanned between the bottoms of faced concave portions 6A and 6B formed on a substrate 5. Moreover, piezoelectric elements 4A to 4D are respectively arranged on one-side plane surfaces of diaphragms 3A to 3D, the diaphragms 3A to 3D are connected to the sides and bottoms of the concave portions 6A and 6B, and a fixing plate 1 is connected to a connection plate 2 so that the longitudinal direction of the fixing plate 1 becomes parallel with the direction for the diaphragms 3A to 3D to hold the connection plate 2, that is, the Y-axis direction.

It is preferable that the members of the fixing plate 1, connection plate 2, diaphragms 3A to 3D, and substrate 5 are connected at the side of each member and formed into one body. By using a green-sheet laminating method to be described later, it is possible to easily obtain the device 31 as an integral body. Though electrode leads are arranged on piezoelectric elements 4A to 4D from electrodes for forming the piezoelectric elements 4A to 4D toward the substrate 5, they are omitted in FIG. 1.

In this case, a fixing plate denotes a component for causing a predetermined displacement by driving a piezoelectric element and a member such as a magnetic head can be set to the fixing plate. Moreover, a connection plate denotes a component for connecting a fixing plate with substrate and diaphragm, and a diaphragm denotes a component for generating a strain with piezoelectric elements arranged on the surface and transmitting the strain to a connection plate. The diaphragm also has a function for transmitting a strain generated due to a displacement of a fixing plate to a piezoelectric element when the strain is transmitted to a diaphragm through a connection plate. The substrate denotes a component for holding a driving portion (such as a connection plate, fixing plate, diaphragm, or piezoelectric element), on which various electrode terminals to be set to a measuring instrument are arranged and being provided for handling in practical use.

A concave portion formed on the substrate need not be a recess having a side vertical to a bottom or must not always have a portion opening in one direction. It is also possible that the bottom and the side have an angular portion having a curvature. That is, the concave portion denotes a portion having one bottom and two sides. For example, a concave portion is formed by cutting out a part of the circumference of a substrate like a quadrangle. Moreover, when a quadrangular hole is formed in the substrate, it is possible to regard three out of four sides as a concave portion. Furthermore, it is possible that the angle between the side and the bottom of a concave portion has an inclination as long as the driving characteristic of a device of the present invention can be obtained.

Figure 12:
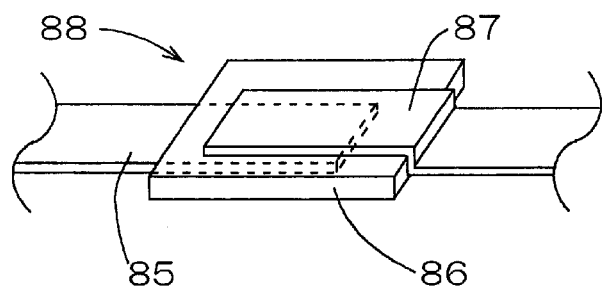
FIG. 12 shows a perspective view of an embodiment of a piezoelectric element arranged on a piezoelectric/electrostrictive device of the present invention.
Figure 13:
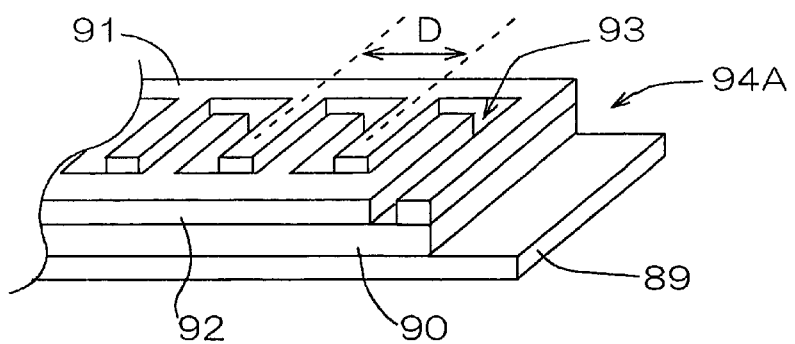
FIG. 13 shows a perspective view of another embodiment of a piezoelectric element arranged on a piezoelectric/electrostrictive device of the present invention.

As a mode of the piezoelectric elements 4A and 4B, a lamination-type piezoelectric element 88 is a typical one, which is obtained by forming a piezoelectric film 86 like a layer by positioning the film 86 between a first electrode 85 and a second electrode 87 as shown in FIG. 12. Moreover, as shown in FIG. 13, it is possible to use a piezoelectric element 94A having a comb-type electrodes structure in which a piezoelectric film 90 is formed on a diaphragm 89 and a first electrode 91 and a second electrode 92 form a predetermined-width gap 93 on the piezoelectric film 90. Furthermore, it is possible to form the first electrode 91 and the second electrode 92 in FIG. 13 at the connection plane between the diaphragm 89 and piezoelectric film 90. Furthermore, as shown in FIG. 14, a piezoelectric element 94B is preferably used in which the piezoelectric film 90 is embedded between the comb-type first electrode 91 and second electrode 92.

Figure 14:
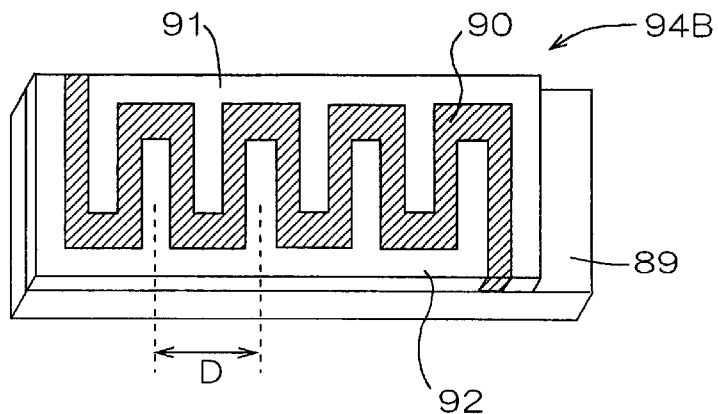
FIG. 14 shows a perspective view of still another embodiment of a piezoelectric element arranged on a piezoelectric/electrostrictive device of the present invention.

When a piezoelectric element having the comb-type electrodes shown in FIGS. 13 and 14 is used, it is possible to increase a displacement by decreasing the pitch D between the comb-type electrodes. The piezoelectric element shown in FIGS. 12 to 14 can be applied to every device of the present invention to be mentioned later.

In the case of the device 31, by applying a voltage to the piezoelectric elements 4A to 4D, a strain corresponding to the applied voltage is generated in the piezoelectric film. The strain is transmitted to the diaphragms 3A to 3D, then to the connection plate 2, and then to the fixing plate 1 and thereby, a predetermined displacement is generated for the fixing plate 1.

Therefore, as shown in FIG. 1, when arranging the piezoelectric elements 4A to 4D on the same-directional plane surfaces of the diaphragms 3A to 3D, by driving one pair of piezoelectric element 4A and 4D which are diagonally located with respect to each other, at the same phase and the other pair of piezoelectric elements 4B and 4C at the opposite phase to the piezoelectric elements 4A and 4D about the joint between the fixing plate 1 and the connection plate 2, that is, about the intersection between X-axis and Y-axis, the piezoelectric elements 4B and 4C are contracted when the piezoelectric elements 4A and 4D are extended, and this state appears as displacement of the diaphragms 3A to 3D on which the piezoelectric elements 4A to 4D are arranged. Therefore, a displacement of in-plane rotation mode about the intersection between X-axis and Y-axis in the plane X-Y shown by the arrow K1 in FIG. 1 is generated for the fixing plate 1.

On the other hand, by driving a set of piezoelectric elements 4A and 4C present at line symmetric positions at the same phase and the other set of piezoelectric elements 4B and 4D at the opposite phase by using Y-axis which is the longitudinal axis of the fixing plate 1 as a symmetric axis, a Y-axis-directional uniaxial shift in the plane X-Y shown by the arrow K2 in FIG. 1 is obtained.

The same phase/opposite phase for driving a piezoelectric element determines the direction of a strain generated in a piezoelectric element. The same phase represents driving a piezoelectric element so that a same-directional strain is obtained, and the opposite phase represents driving a piezoelectric element so that a reverse-directional strain is obtained or not driving a piezoelectric element without adding a signal, that is, driving a piezoelectric element so that a relatively-opposite-directional strain is obtained. Therefore, it is possible to constitute a group of piezoelectric elements by properly combining piezoelectric elements using the transversal effect ($d_{31}$) of an electric-field-induced strain and piezoelectric elements using the longitudinal effect ($d_{33}$) of the electric-field-induced strain. Moreover, by constituting a piezoelectric element with a piezoelectric material requiring a polarization operation, it is possible to control a phase by setting the direction of a signal under driving to the direction same as or opposite to the polarity under polarization even for piezoelectric elements using all the same $d_{33}$ or $d_{31}$.

Like this, because the device 31 has a structure in which the displacement of the connection plate 2 obtained by magnifying the displacement of the piezoelectric elements 4A to 4D is further magnified as the displacement of the fixed plate 1, it is possible to optionally set a response speed and the front-end displacement amount or generation force of the fixing plate 1 by variously selecting the length of the connection plate 2 and the length of the fixed plate.

In the case of the device 31 for generating the above displacement on the fixing plate 1, it is preferable that the device 31 is connected with the connection plate 2 at the longitudinal center of the fixing plate 1 and the connection plate 2. In this case, because a displacement can be easily controlled, it is possible to obtain the maximum magnification rate of displacement.

Moreover, in the case of the device 31, it is not necessary for all of the diaphragms 3A to 3D and piezoelectric elements 4A to 4D to have the same shape. For example, it is also possible to generate the above-described uniaxial for the fixing plate 1 by decreasing the Y-axis-directional lengths of the diaphragms 3A and 3C and piezoelectric elements 4A and 4C but increasing the Y-axis-directional lengths of the diaphragms 3B and 3D and piezoelectric elements 4B and 4D. In the same manner, it is possible to generate an in-plane rotation displacement for the fixing plate 1 by decreasing the Y-axis-directional lengths of the diaphragms 3A and 3D and piezoelectric elements 4A and 4D but increasing the Y-axis-directional lengths of the diaphragms 3B and 3C and piezoelectric elements 4B and 4C.

Furthermore, it is possible to generate an in-plane rotation displacement for the fixing plate 1 by using a structure in which a slit parallel with the X-axis direction is provided for the diaphragms 3A and 3D but neither piezoelectric elements 4A nor 4D are provided for them or a structure in which neither diaphragms 3A nor 3D are used and driving the piezoelectric elements 4B and 4C at the same phase. Furthermore, it is possible to generate an axial displacement of the fixing plate 1 by using a structure in which a slit parallel with the X-axis direction is provided for the diaphragms 3A and 3C but neither piezoelectric elements 4A nor 4C are provided for them or a structure in which neither diaphragms 3A nor 3D are used and driving the piezoelectric elements 4B and 4D at the same phase.

In the case of the device 31, the piezoelectric elements 4A to 4D are provided for only one-side plane surfaces of the diaphragms 3A to 3D. However, it is also preferable to arrange piezoelectric elements on the other-side plane surfaces. In this case, it is needless to say that every piezoelectric element can be used for driving. It is possible to use the piezoelectric elements on one-side plane surfaces to drive the fixed plate 1 and those on the other-side plane surfaces as auxiliary elements. In this case, an auxiliary element represents a troubleshooting element, displacement confirmation/decision element, driving support element, or the like. By using an auxiliary element, it is possible to accurately drive a fixing plate.

Auxiliary elements can be arranged also by forming the piezoelectric elements 4A to 4D provided for one-side plane surfaces of the diaphragms 3A to 3D as one pair of two elements divided in the X-axis direction. In this case, piezoelectric elements at the side close to the joint between the fixing plate 1 and connection plate 2 are used as driving elements and the others are used as auxiliary elements. To divide one piezoelectric element, it is possible to use either of a method of arranging one piezoelectric element and thereafter dividing it through laser-beam machining and a method of first dividing one piezoelectric element into pairs of elements and then arranging them. Moreover, it is also preferable to arrange a plurality of piezoelectric elements on one diaphragm and control shifts and vibrations.

Furthermore, it is possible to set a piezoelectric element to the substrate 5 when it cannot be overhung to the connection plate 2. It is needless to say that modes of the above diaphragms and piezoelectric elements can be used by variously combining them.

Figure 2:
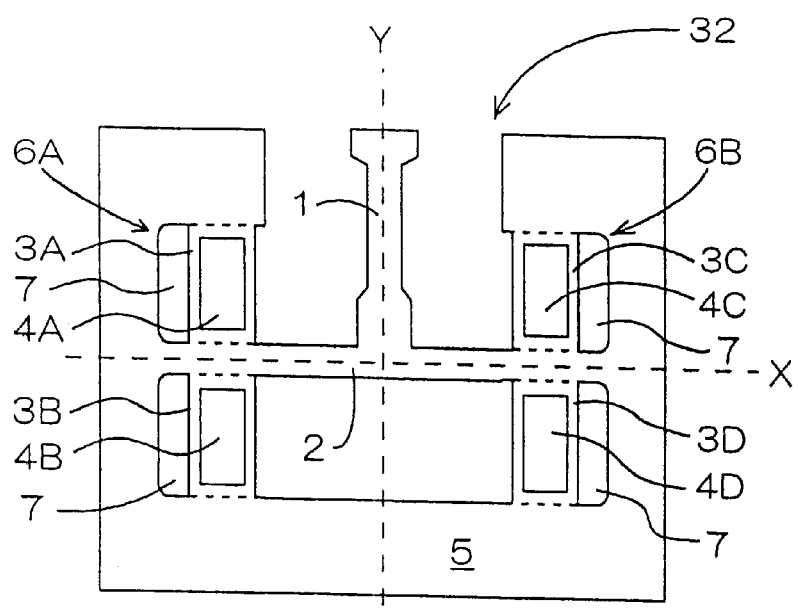
FIG. 2 shows a top view of another embodiment of a piezoelectric/electrostrictive device of the present invention.

The top view of FIG. 2 shows another embodiment of a device of the present invention. In the case of a device 32, diaphragms 3A to 3D are respectively connected with only the sides of concave portions 6A and 6B, but they are not connected with the bottoms of the concave portions 6A and 6B. A gap 7 is formed between the bottoms of the concave portions 6A and 6B on one hand and the diaphragms 3A to 3D on the other respectively. Thus, it is enough that the diaphragms 3A to 3D are connected with the sides of the concave portions 6A and 6B in the direction (Y-axis direction) for at least the diaphragms 3A to 3D to hold the connection plate 2. In this case, there is an advantage that a uniaxial shift of a fixed plate 1 toward Y-axis can be made purer compared to the case of the above device 1.

As clarified by comparing the shape of the fixing plate 1 of the device 31 with that of the fixing plate 1 of the device 32, the shape of the fixing plate 1 is not restricted. It is possible to set the shape of the fixing plate 1 by considering the shape and weight of an element or sensor to be set to the front end of the fixing plate 1.

Figure 3:
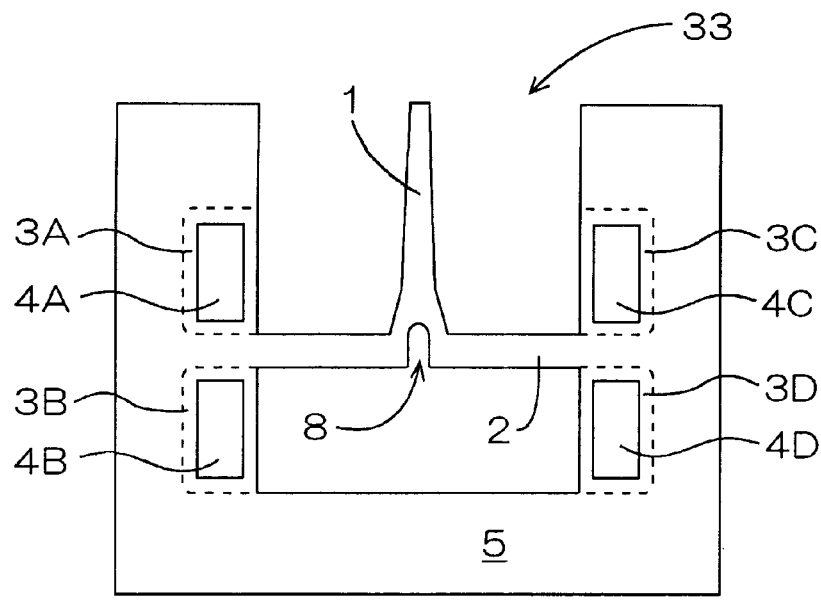
FIG. 3 shows a top view of still another embodiment of a piezoelectric/electrostrictive device of the present invention.

FIG. 3 shows a top view of still another embodiment of a device of the present invention. A device 33 has a structure in which a notch 8 is provided for the joint between the fixing plate 1 and the connection plate 2 of the device 31. In this case, it is possible to more efficiently convert a displacement of the connection plate into an in-plane rotation displacement of the fixing plate 1 compared to the case of the device 31. That is, the in-plane rotation displacement of the fixing plate 1 of the device 31 previously shown in FIG. 1 is mainly generated in accordance with a bending displacement in the plane X-Y of the connection plate 2. Therefore, the in-plane rotation displacement is a displacement in which a connection angle between the connection plate 2 and the fixing plate 1 is almost kept. However, when the notch 8 is formed like the case of the device 33 shown in FIG. 3, it is possible to convert a bending displacement of the connection plate 2 into a rotation displacement for further changing connection angles between the fixing plate 1 and the connection plate 2 at the connection position between the connection plate 2 and the fixing plate 1. As a result, it is possible to increase a displacement of the fixing plate 1. That is, the device 31 shown in FIG. 1 is used by magnifying displacement of the piezoelectric elements 4A to 4D mainly into a bending displacement of the connection plate 2 and the device 33 shown in FIG. 3 has a structure in which a displacement magnified to a bending displacement of the device 33 is further magnified as a rotation displacement, in a way, a two-step magnification mechanism can be effectively shown. It is preferable to form the notch 8 so as to increase the width-directional distance of the connection plate 2, that is, the Y-axis-directional distance up to the inside the fixing plate 1 and it is preferable to decrease the width of the notch 8, that is, the X-axis-directional distance of the notch 8.

Figure 4:
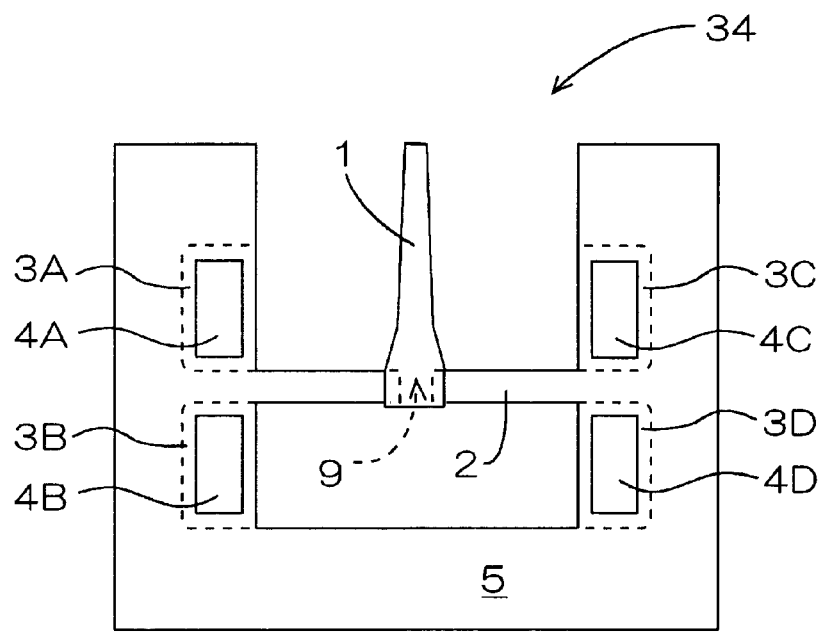
FIG. 4 shows a top view of still another embodiment of a piezoelectric/electrostrictive device of the present invention.

FIG. 4 shows a top view of still another embodiment of a device of the present invention. The arranged state of diaphragms of a device 34 is the same as the case of the device 32 described above. However, the device 34 has a structure in which a connection plate 2 is divided into two plates in the X-axis direction which is the spanning direction of the connection plate 2, a gap 9 is formed at the central portion of the connection plate 2, and a fixing plate 1 is connected to the plane surface of the connection plate 2 so as to cross the gap 9.

Thus, by preparing the fixing plate 1 as a separate body, such an advantage is obtained that it is possible to widen the range for selecting the material and shape of the fixing plate 1 according to the purpose of use. However, because the connection plate 2 must be connected with the fixing plate 1 by an adhesive or the like, the reliability is slightly deteriorated. Moreover, in the case of the device 34, it is possible to form a notch 8 the same as that of the device 33 at an end of the fixing plate 1 at a position crossing the divided connection plate 2, that is, at the gap 9.

Figure 5:
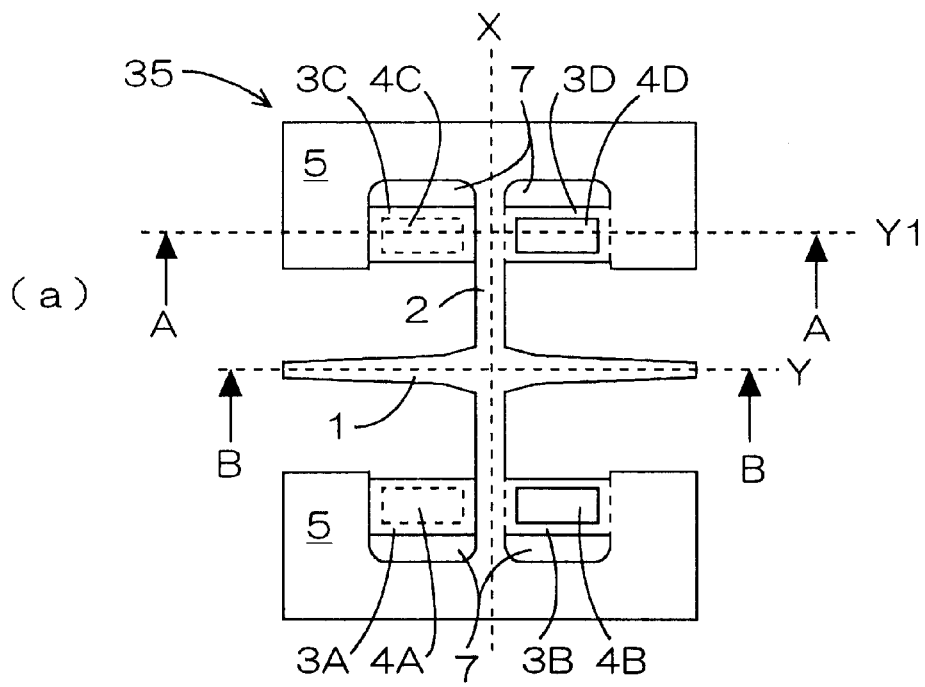
FIG. 5 show a top view, sectional view, and shift illustration of still another embodiment of a piezoelectric/electrostrictive device of the present invention.
Figure 5:
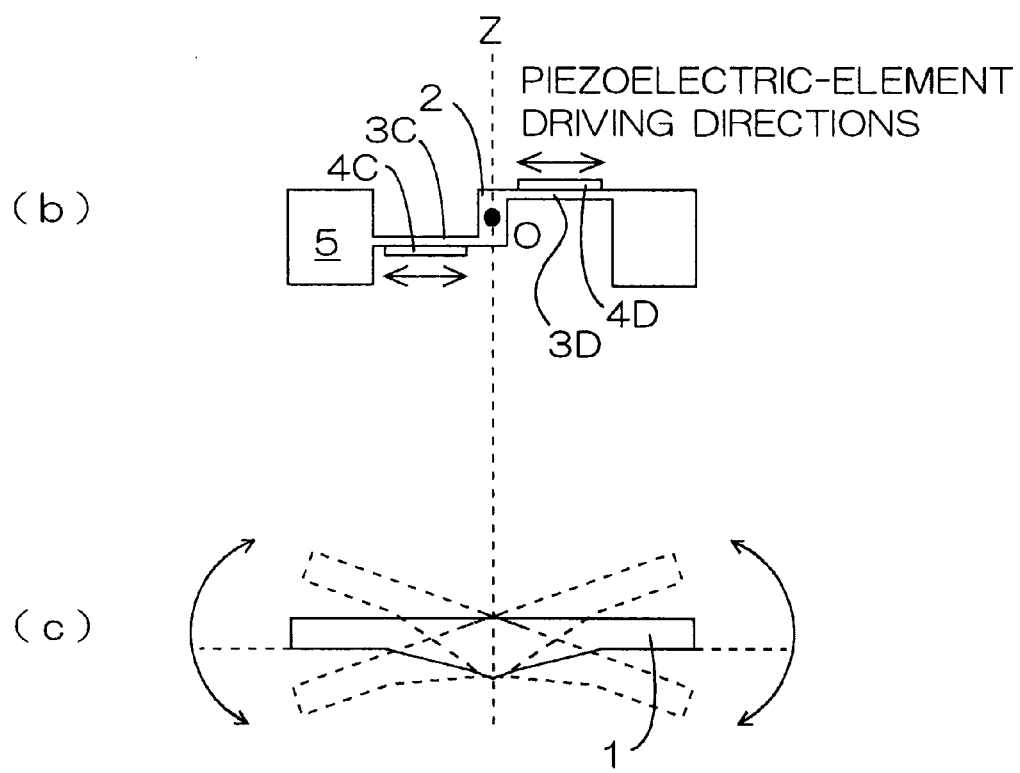

FIG. 5(a) shows a top view of still another embodiment of a device of the present invention. A device 35 has a structure in which a fixing plate 1 is connected to a connection plate 2 so as to intersect with the connection plate 2. By using the above structure, it is possible to greatly increase displacement at both ends of the fixing plate 1 and attach an element or sensor to both ends.

FIG. 5(b) is an arrow-AA view at the Y1 axis, in which a pair of diaphragms (diaphragms 3C and 3D) for holding the connection plate 2 are each connected with the connection plate 2 at positions shifted in the thickness direction (Z-axis direction) of the connection plate 2. In this case, by arranging piezoelectric elements 4C and 4D on one-side plane surfaces of the diaphragms 3C and 3D by using the middle point O of the connection position between a pair of diaphragms (diaphragms 3C and 3D) for holding the connection plate 2 on one hand and the connection plate 2 on the other as a point-symmetric center and moreover, driving these piezoelectric elements 4C and 4D at the same phase, it is possible to generate a rotation displacement about the longitudinal-directional axis (X-axis) of the connection plate 2 as shown by the arrow-BB view on Y-axis shown in FIG. 5(c).

Figure 6:
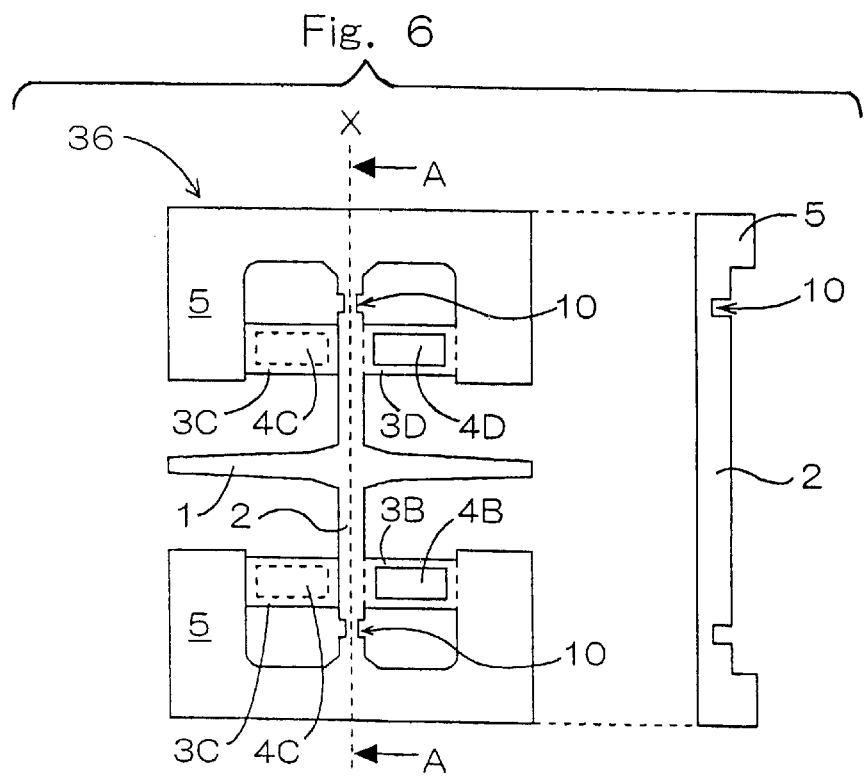
FIG. 6 shows a top view and a sectional view of still another embodiment of a piezoelectric/electrostrictive device of the present invention.

FIG. 6(*a*) shows a top view of a device 36 in which a notch 10 is formed on a connection plate 2 between the connection part of the connection plate 2 and the substrate 5 and the connection part of the connection plate 2 and the diaphragms 3A to 3D and FIG. 6(*b*) shows an arrow-AA view on X-axis. By forming the notch 10, it is possible to efficiently operate a fixing plate 1. When forming the notch 10, the operation efficiency is further improved by decreasing the thickness of the connection plate 2. The shape of the notch 10 is not restricted as long as the width and/or thickness of the notch 10 is decreased.

Figure 7:
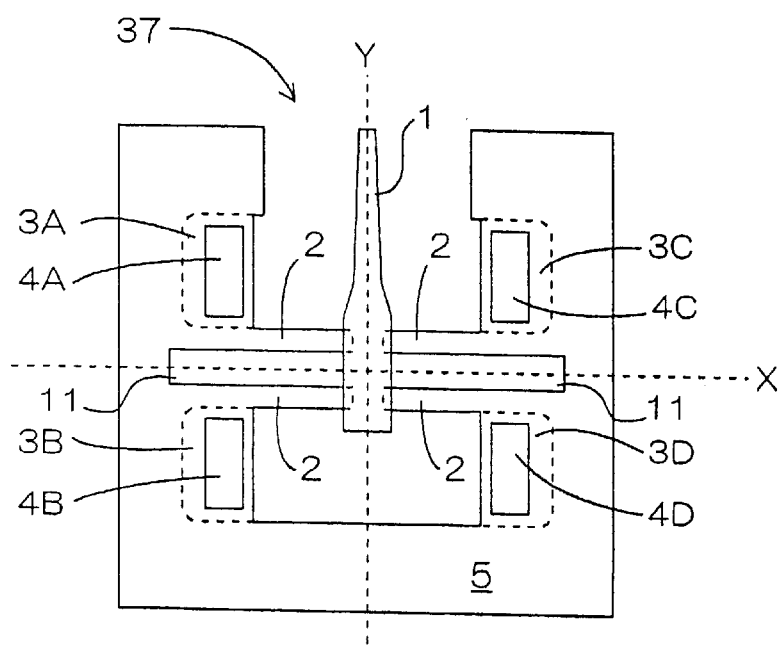
FIG. 7 shows a top view of still another embodiment of a piezoelectric/electrostrictive device of the present invention.

A device 37 shown in FIG. 7 has a mode in which a connection plate 2 is divided into two plates in the longitudinal direction (Y-axis direction) of a fixing plate 1 and moreover, each of the divided connection plates 2 is divided into two plates in the spanning direction of each connection plate 2. Therefore, the fixing plate 1 is connected to either-side plane of the connection plate 2 so as to resultantly cross four connection plates 2. In this case, it is needless to say that the connection plates 2 and the fixing plate 1 can be integrally formed and the connection plate 2 can be divided into three parts or more. The division of a connection plate in the longitudinal direction (Y-axis direction) of a fixing plate in the case of the present invention also includes a case in which a plurality of connection plates are arranged in the Y-axis direction through a gap without changing Y-axis-directional widths of the connection plates in addition to a case in which a connection plate is divided and a gap is formed and thereby, the Y-axis-directional width of newly formed connection plates is decreased.

The device 37 has a mode in which piezoelectric elements 4A to 4D respectively drive one connection plate 2 through corresponding diaphragms 3A to 3D. Therefore, it is possible to obtain a plurality of points (joints) for making strains of the piezoelectric elements 4A to 4D work on the fixing plate 1. For example, by driving the piezoelectric elements 4A and 4D at the same phase and the piezoelectric elements 4B and 4C at a phase opposite to the case of the piezoelectric elements 4A and 4D, it is possible to make the fixing plate 1 efficiently generate a displacement of in-plane rotation mode.

Moreover, by driving the piezoelectric elements 4A and 4C at the same phase and the piezoelectric elements 4B and 4D at a phase opposite to the case of the piezoelectric elements 4A and 4C, it is possible to obtain a displacement of Y-axis-directional uniaxial mode. In this case, because a gap 11 is formed between the connection plates 2 in the Y-axis direction, it is possible to obtain a pure displacement mode compared to the case of the above device 31 or the like.

Furthermore, it is possible to span a flat member thinner than the connection plates 2 between the connection plates 2 in the Y-axis direction. In this case, though the relative displacement amount of the fixing plate 1 decreases compared to the case of not spanning the flat member, it is possible to operate the fixing plate 1 at a higher response speed because the rigidity is improved. Furthermore, it is not always necessary to form the gap 11 over the entire length (X-axis-directional length) of the connection plate 2. Even if the gap 11 is formed on at least a part in the connection plate 2, the advantage of the gap 11 can be obtained.

Figure 8:
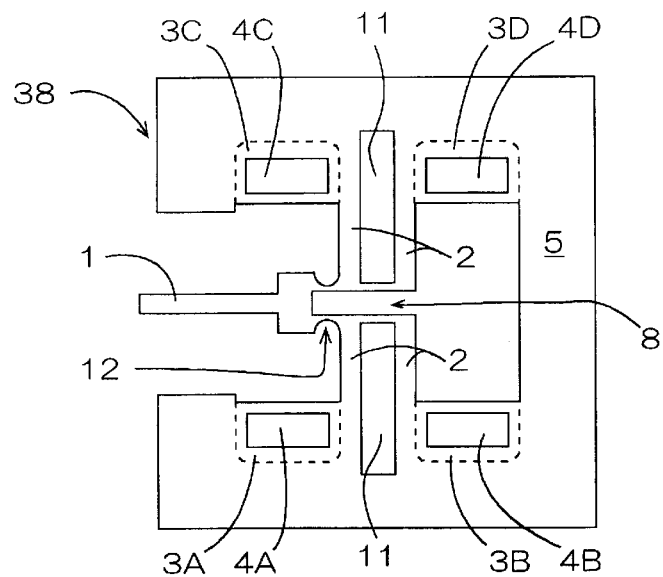
FIG. 8 shows a top view of still another embodiment of a piezoelectric/electrostrictive device of the present invention.

FIG. 8 shows a top view of a device 38 in which a fixing plate 1 is integrally connected to two connection plates formed by being divided in the longitudinal direction of the fixing plate 1, a hinge portion 12 is provided for the fixing plate 1 from the joint between the fixing plate 1 and a connection plate 2 toward the longitudinal direction of the fixing plate 1, and moreover a notch 8 is formed on the joint between the fixing plate 1 and the connection plate 2. By forming the hinge portion 12 simultaneously with the notch 8 in order to assist generation of a displacement of in-plane mode of the fixing plate 1, it is possible to more effectively obtain a larger displacement in-plane rotation mode. It is needless to say that the above hinge portion 12 can be formed on the above devices 31 to 37.

Figure 9:
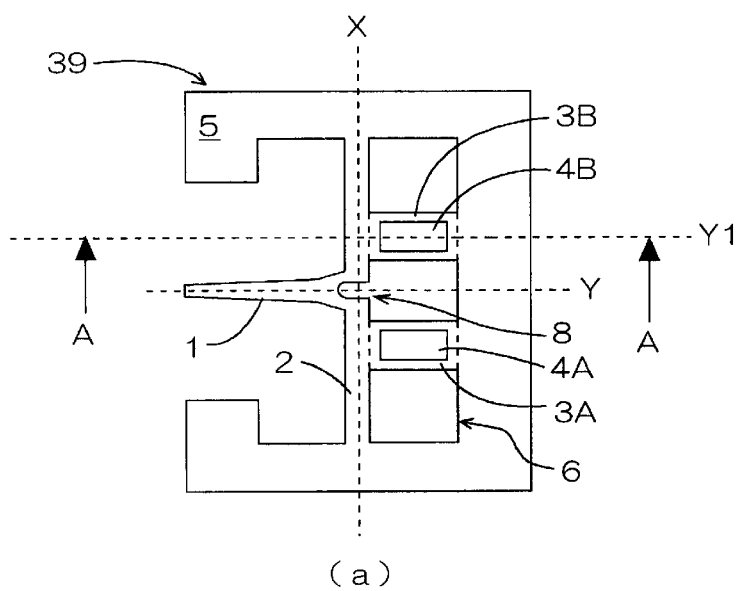
FIG. 9 show a top view and sectional view of still another embodiment of a piezoelectric/electrostrictive device of the present invention.
Figure 9:
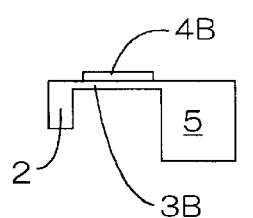
Figure 9:
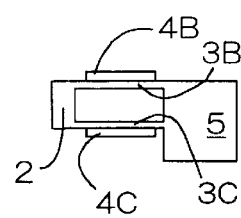
Figure 9:
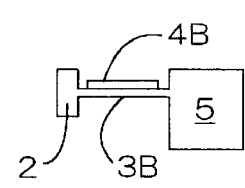

FIG. 9 shows still another embodiment of a device of the present invention. A device 39 is a mode in which the diaphragms 3A and 3C are removed from the above described device 32 when using two diaphragms 3A and 3B as shown in FIG. 9(*a*). That is, the device 39 has a structure in which a connection plate 2 is spanned between the sides of a concave portion 6 formed on a substrate 5, two diaphragms 3A and 3B on which piezoelectric elements 4A and 4B are arranged are spanned between the connection plate 2 and the bottom of the concave portion 6 of the substrate 5, and a fixing plate 1 is connected to the connection plate 2 so that the longitudinal direction of the fixing plate 1 becomes parallel with the spanning direction (Y-axis direction) of the diaphragms 3A and 3B. The diaphragms 3A and 3B are normally arranged at positions symmetric to the longitudinal-direction axis (Y-axis) of the fixing plate 1. Moreover, it is possible to span two diaphragms or more between the connection plate 2 and the bottom of the concave portion 6.

FIGS. 9(*b*) to 9(*d*) show an arrow-AA view on the Y1 axis showing a mode of the diaphragm 3B preferably adopted for the device 39. The mode of the diaphragm 3B is also applied to the diaphragm 3A. FIG. 9(*b*) shows a mode in which the diaphragm 3B is spanned between the vicinities of the surfaces of the connection plate 2 and the substrate 5.

Moreover, FIG. 9(*c*) shows a structure in which a pair of diaphragms 3B and 3C constituted so that plane surfaces each other and are spanned between the connection plate 2 and the substrate 5. In this case, another diaphragm 3D is provided for the diaphragm 3A so as to form a pair, and the fixing plate is driven by the total of four diaphragms. In the case of the above structure, by driving the piezoelectric elements 4B and 4C at the same phase and the piezoelectric elements 4A and 4D (piezoelectric elements to be arranged on a not-illustrated diaphragm 3D) at a phase opposite to the case of the piezoelectric elements 4B and 4C, it is possible to predominantly generate a displacement of in-plane rotation mode for the fixing plate 1. Moreover, by driving all the piezoelectric elements 4A to 4D at the same phase, it is possible to predominantly generate a displacement of uniaxial mode. Thus, compared to the case of using two diaphragms/piezoelectric elements, it is possible to suppress a Z-axis-directional shift of the fixing plate 1 and moreover, an advantage is obtained that a displacement amount and generation force of the fixing plate 1 can be set to large values. As described above, it is possible to arrange two or more pairs of diaphragms constituted so that the plane surfaces face each other correspondingly to the fact that two or more diaphragms can be spanned between the connection plate 2 and the bottom of the concave portion 6.

FIG. 9(*d*) shows a mode in which the diaphragm 3B is arranged at the central portion of the connection plate 2 in its thickness direction. In this case, it is preferably possible to set the action point to the connection plate 2 of the piezoelectric element 4B (diaphragm 3B) to the position of center of gravity of the connection plate 2. Therefore, it is preferably possible to decrease the Z-axis-directional shift of the fixing plate 1.

The modes of a diaphragm shown in FIGS. 9(c) and 9(d) can be applied to other embodiments for holding a connection plate. That is, when applying the mode in FIG. 9(c) to other embodiments, a connection plate is held by a pair of diaphragms facing in the thickness direction of the connection plate. When applying the mode in FIG. 9(d) to other embodiments, a connection plate is held by two diaphragms at the central portion of the connection plate in its thickness direction.

Figure 17:
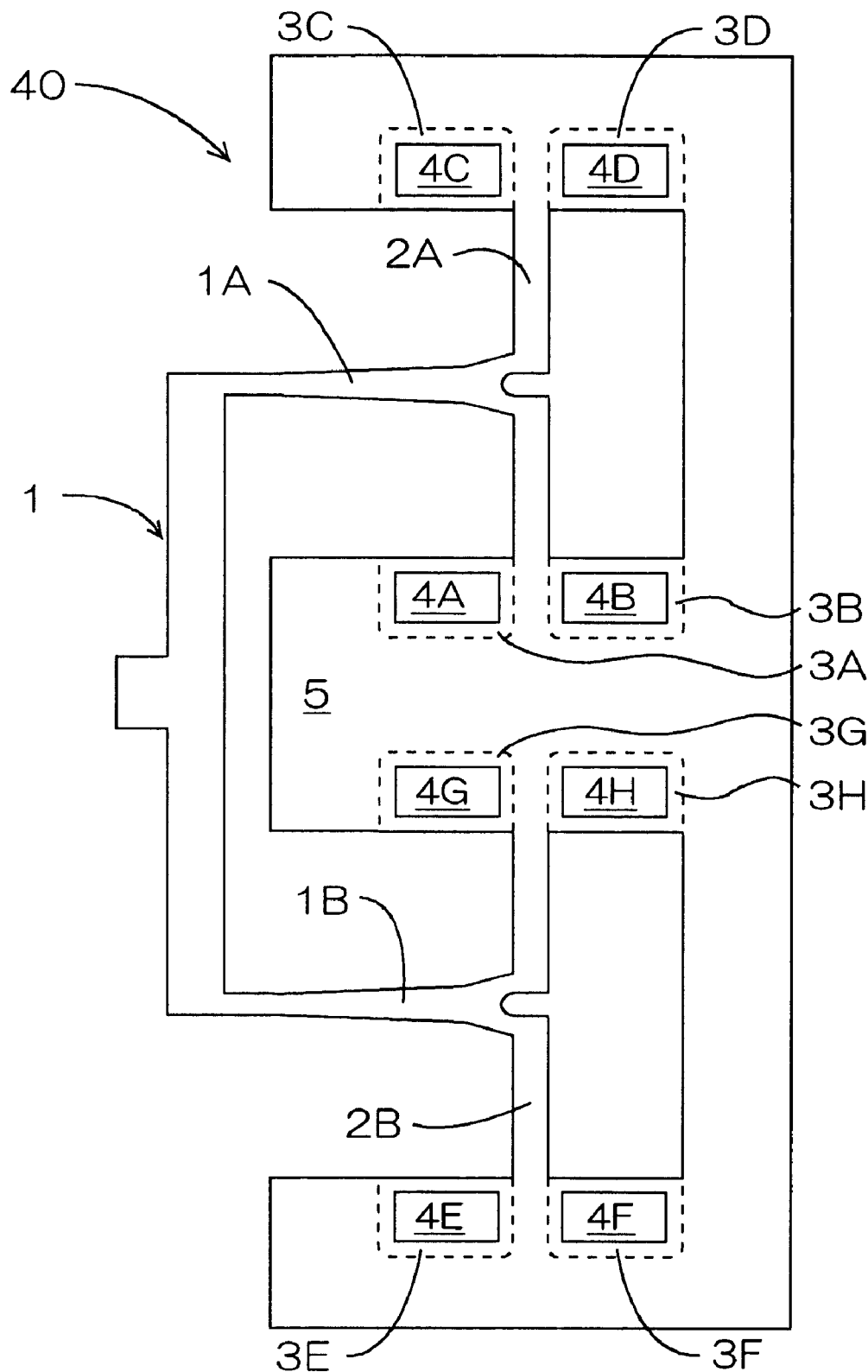
FIG. 17 shows a top view of still another embodiment of a piezoelectric/electrostrictive device of the present invention.

Then, FIG. 17 shows a top view of a device 40 constituted by connecting two devices 33 shown in FIG. 3 previously described. In the case of the device 40, a fixing plate 1A driven by piezoelectric elements 4A to 4D is connected with a fixing plate 1B driven by piezoelectric elements 4E to 4H and thus, an integral fixing plate 1 is formed. By using the structure, it is possible to generate a large amount of displacement and moreover increase the driving force of the device. Therefore, when securing other devices such as various sensors and magnetic heads to the fixing plate, it is easy to properly select the structure of the device 33 or the structure of the connected device 40 in accordance with the size or mass of the device.

Moreover, the device 40 has features of reducing unnecessary residual vibrations of the fixed plate 1 generated under a high-speed operation by driving one connected device (e.g. fixed plate-1B side) for braking at a predetermined timing and realizing high-speed positioning from the viewpoint of controlling a displacement and vibration.

Figure 18:
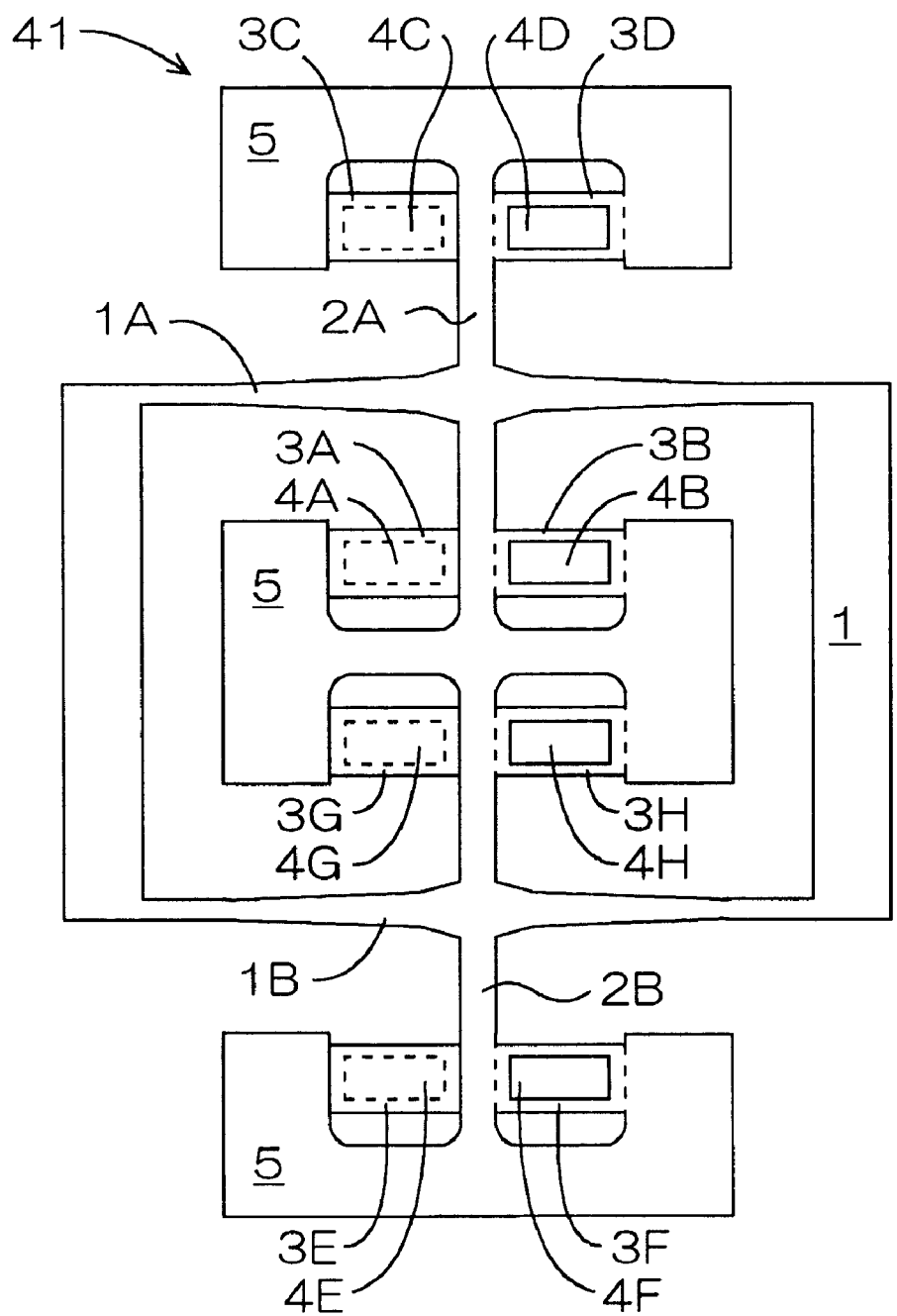
FIG. 18 shows a top view of still another embodiment of a piezoelectric/electrostrictive device of the present invention.

The above connection between devices is not restricted to the case of using the device 33. This can be applied to the devices 31 to 39 shown in FIGS. 1 to 9. For example, a device 41 shown by a top view in FIG. 18 is constituted by connecting the device 35 shown in FIG. 5. Therefore, it is possible to generate a displacement of the rotation mode about the longitudinal axis of the connection plates 2A and 2B, increase a driving force, and brake the motion of the fixing plate 1.

Figure 19:
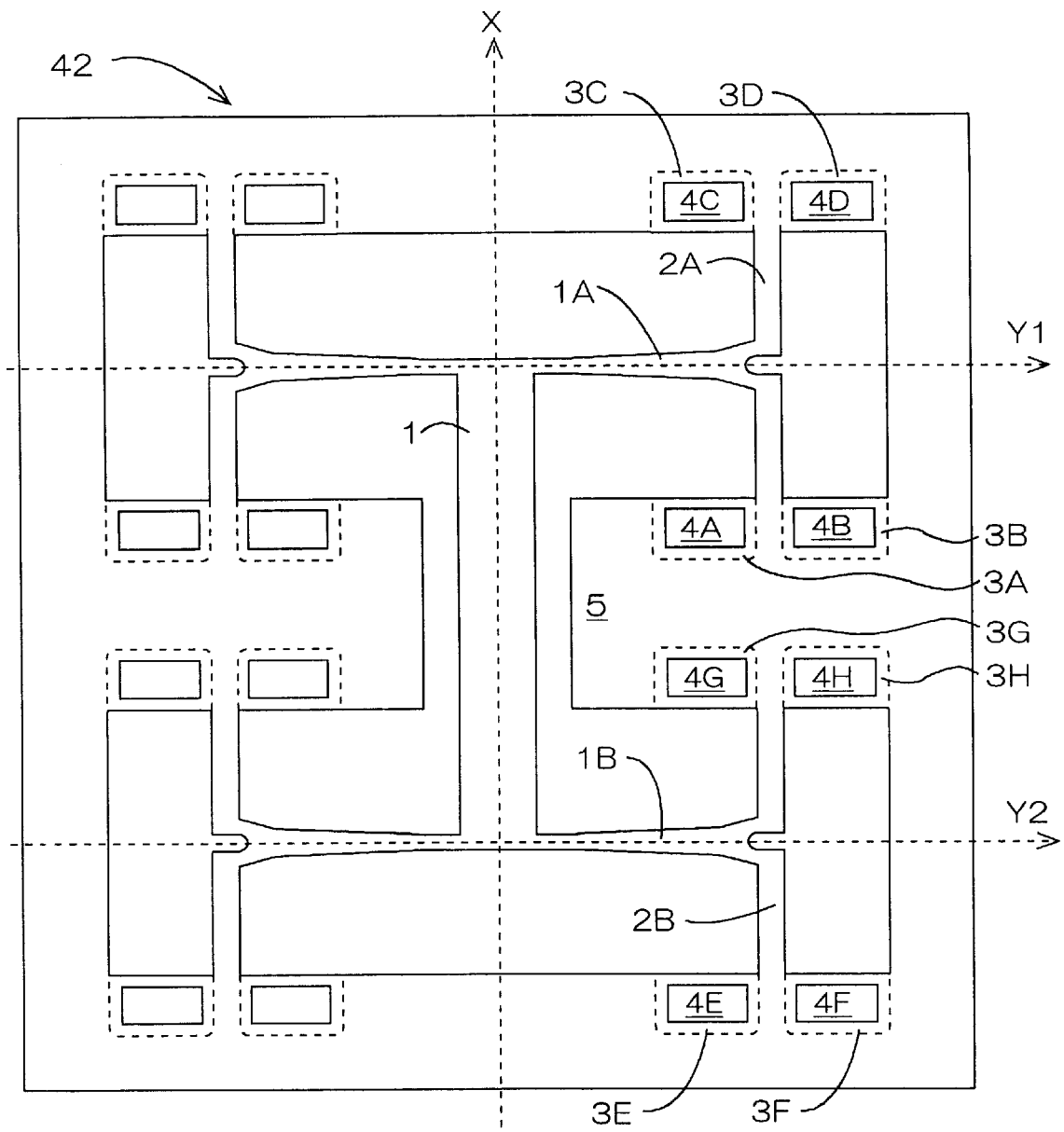
FIG. 19 shows a top view of still another embodiment of a piezoelectric/electrostrictive device of the present invention.

The connection between devices described above is not restricted to the connection between two devices. It is also possible to connect two devices or more by considering an embodiment. As an example, FIG. 19 shows a top view of a device 42 obtained by connecting four devices 33 shown in FIG. 3. The device 42 has, in other words, a structure obtained by connecting two devices 40 shown in FIG. 17 so that they are symmetric to the X-axis. By using this structure, it is possible to generate purer X-axis-directional and Y-axis(Y1-axis and Y2-axis)-directional displacement with a large force.

Embodiments of the present invention are described above mainly on the structures of devices, in which various displacement modes of a fixing plate, that is, the in-plane rotation displacement mode, uniaxial displacement mode, and rotation displacement mode represent that the displacement direction of the fixing plate is predominant in each described direction but having directional components other than the above is not completely excluded. When considering a case of applying a device of the present invention to a magnetic head, it is preferable to use a three-dimensional shiftlessness or a uniaxial displacement and in-plane rotation displacement so as to keep the interval (gap) between a head and a recording medium constant.

In the case of the above-mentioned various devices, a piezoelectric element has a unimorph structure. However, it is also possible for a piezoelectric element to have a bimorph structure. Moreover, it is needless to say that the number of diaphragms or the number of piezoelectric elements to be arranged can be optionally selected as long as it is not deviated from the design rules of the above devices. Furthermore, a device of the present invention is, as described above, not only used as an active element such as a displacing element or a vibrator to be driven by a piezoelectric element, but also used for various sensors as a passive element such as an acceleration sensor or impact sensor. Particularly, in the case of detection of acceleration, it is possible to easily improve the detection sensitivity by providing an inertial mass such as a weight for the front end of a fixing plate to increase the weight of the front end.

Figure 10:
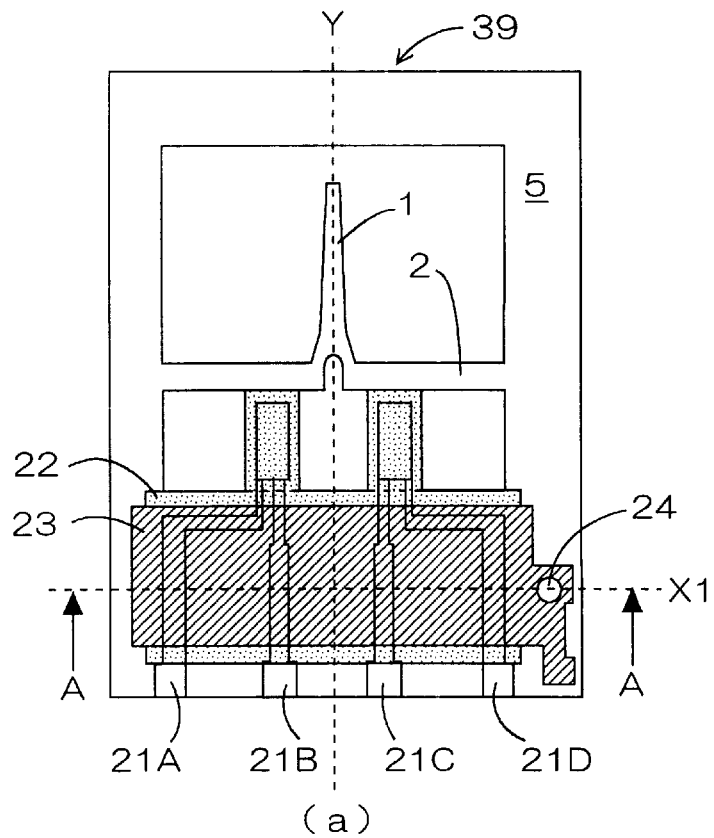
FIG. 10 show a top view and a sectional view of a mode having a detailed structure of the piezoelectric/electrostrictive device shown in FIG. 9.
Figure 10:
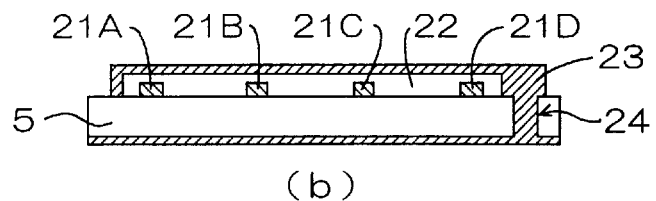
Figure 10:
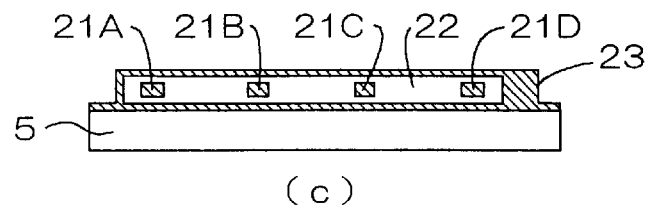
Figure 10:
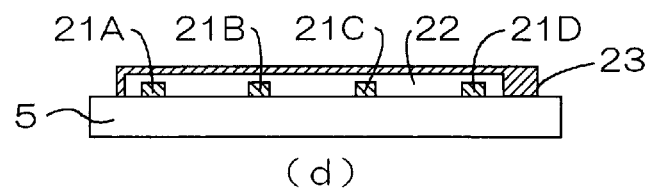

Then, a mode for forming an electrode lead from a piezoelectric element is described below by using the above device 39 as an example. FIG. 10(a) shows a top view of an embodiment in which electrode leads 21A to 21D are provided for piezoelectric elements 4A and 4B arranged on the device 39, an insulating coating layer 22 is provided for the piezoelectric elements 4A and 4B and the electrode leads 21A to 21D, and moreover a shielding layer 23 is formed so as to cover the insulating coating layer 22. FIGS. 10B to 10D are arrow-AA views on the X1 axis in FIG. 10(a), showing different embodiments.

The insulating coating layer 22 has a function for effectively preventing the piezoelectric elements 4A and 4B and the electrode leads 21A to 21D from being short-circuited when using a fixing plate 1 and/or the piezoelectric elements 4A and 4B in a liquid environment or a humidified environment. The shielding layer 23 has functions for cutting off external electromagnetic waves to preferably secure a displacing accuracy when operating a device at a high frequency or when detecting high-frequency vibrations and moreover, preventing erroneous operation and noise.

Modes for arrangement of the shielding layer 23 include not only a mode for forming a substrate 5 so as to hold the substrate 5 as shown in FIG. 10(b) but also a mode for enclosing only the wiring portion on the substrate 5 as shown in FIG. 10(c) and a mode for shielding the wiring portion with only the upper-piece side as shown in FIG. 10(d). Particularly, the modes for entirely shielding the wiring portion are preferable as shown in FIGS. 10(b) and 10(c). In FIG. 10(a), electrical connection of the shielding layer 23 formed on each face of the substrate 5 is secured by using a through-hole 24 formed on the substrate 5. However, it is also possible to secure the electrical connection by using the sides of the substrate 5. Details of materials preferably used to form the insulating coating layer 22 and shielding layer 23 are described together with device-forming materials to be mentioned later.

Then, materials used for a device of the present invention are described. Ceramics is preferably used for a substrate, fixing plate, connection plate, and diaphragm. For example, fully-stabilized zirconia, partially-stabilized zirconia, alumina, magnesia, and silicon nitride are listed. Among them, full-stabilized zirconia and partially-stabilized zirconia are most preferably used because they have a large mechanical strength, a high toughness, and a small reactivity with a piezoelectric material and electrode materials even in the form of a thin plate. When using fully-stabilized zirconia or partially-stabilized zirconia as the material of the substrate and the like, it is preferable to add an additive such as alumina or titania to at least the diaphragm.

Moreover, when using ceramics, it is possible to integrally form a device by the green-sheet laminating method to be described later. Therefore, ceramics preferable from the viewpoints of securing the reliability of the integration between portions and simplifying the device fabrication process.

It is already described that the thickness and shape of a fixing plate of a device of the present invention are not restricted and therefore, the fixing plate is properly designed in accordance with its purpose. Moreover, the thickness of a substrate is properly determined by considering the operability. However, it is preferable to set the thickness of a diaphragm to 3 to 20 μm and the total thickness of a diaphragm and a piezoelectric element to 15 to 60 μm. Moreover, it is preferable to set the thickness of a connection plate to 20 to 600 μm, the width of the connection plate to 30 to 500 μm, and the aspect ratio [width (Y-axis-directional length)/thickness {Z-axis(axis vertical to both X- and Y-axes)-directional length}] of the connection plate in a range of 0.1 to 15. Particularly, it is preferable to set the aspect ratio in a range of 0.1 to 7 in order to make a displacement in the plane X-Y more predominant.

A piezoelectric ceramics formed like a film is preferably used as a piezoelectric film of a piezoelectric element. Moreover, it is possible to use electrostrictive ceramics, ferroelectric ceramics, or anti-ferroelectric ceramics. Furthermore, it is possible to use a material requiring or not requiring polarization. For a magnetic: recording head, however, it is preferable to use a material having a small strain hysteresis because the linearity between the displacement amount of a fixing plate and a applying voltage or output voltage is important. Therefore, it is preferable to use a material of 10 kV/mm or less as a coercive electric field.

As specific piezoelectric ceramics, the following are listed: lead zirconate, lead titanate, lead magnesium niobate, lead nickel niobate, lead zinc niobate, lead manganese niobate, lead antimony stannate, lead manganese tungstate, lead cobalt niobate, and barium titanate, and ceramics containing a component obtained by combining any ones of the above material. Among them, the present invention preferably uses a material consisting essentially of lead zirconate, lead titanate, and lead magnesium niobate as a major component. This is because that material has a high electromechanical coupling factor, a high piezoelectric constant, and a small reactivity with a substrate (ceramic substrate) when sintering a piezoelectric film, and makes it possible to stably form an object having a predetermined composition.

Moreover, it is possible to add any one of oxides of lanthanum, calcium, strontium, molybdenum, tungsten, barium, niobium, zinc, nickel, manganese, cerium, cadmium, chromium, cobalt, antimony, iron, yttrium, tantalum, lithium, bismuth, and tin, or combination of any ones of the above oxides, or compound that contain any ones of the above element, to the above ceramics. For example, it is also preferable to use a material consisting essentially of lead zirconate, lead titanate, and lead magnesium niobate as a major component and containing lanthanum and strontium by adjusting the coercive electric field or piezoelectric characteristic.

Moreover, it is preferable that the electrode of a piezoelectric element is constituted by a metal that is kept solid-state at room temperature and superior in conductivity. For example, it is a single metal such as aluminum, titanium, chromium, iron, cobalt, nickel, copper, zinc, niobium, molybdenum, ruthenium, palladium, rhodium, silver, tin, tantalum, tungsten, iridium, platinum, gold, or lead or an alloy made by combining any ones of these metals. Moreover, it is possible to use cermet made by dispersing the material of a piezoelectric film or diaphragm in the above metals.

The material of the electrode of a piezoelectric element is determined depending on a piezoelectric-film forming method. For example, to form a first electrode on a diaphragm and then, a piezoelectric film on the first electrode through heat-treatment (firing), it is necessary to use a metal having high melting point such as platinum that is not changed at a firing temperature for the first electrode. However, because a second electrode formed on a piezoelectric film after the piezoelectric film is sintered can be formed at a low temperature, it is possible to use a metal having low melting point such as aluminum.

Moreover, it is possible to form a piezoelectric element by co-firing (firing at one time for integration). In this case, however, it is necessary to use a metal withstanding the sintering temperature of a piezoelectric film for both first and second electrodes. On the other hand, as shown in FIG. 13, to form first and second electrodes 91 and 92 on a piezoelectric film 90, it is possible to form the electrodes 91 and 92 by using the same metal having low-melting point. Thus, it is possible to properly select preferable electrodes as first and second electrodes by depending on a piezoelectric-film forming temperature represented by a piezoelectric-film sintering temperature and a piezoelectric-element structure. Moreover, an electrode lead can be formed simultaneously with an electrode of a piezoelectric element. Furthermore, it is possible to form an electrode lead on a diaphragm simultaneously with a piezoelectric element and then, form an electrode lead on a substrate by various methods such as the sputtering method and screen printing method.

Then, insulating glass or resin is used as the material of an insulating coating layer to be formed on a piezoelectric element and an electrode lead. To improve the performance of a device so as not to decrease a displacement amount, it is preferable to use resin rather than glass. Therefore, one of the following fluorocarbon polymer superior in chemical stability is preferably used: polytetrafluoroethylene based Teflon (Teflon PTFE made by Du Pont), polytetrafluoroethylene-hexafluoro-propylene copolymer based Teflon (Teflon FEP), polytetrafluoroethylene-perfluoroalkylvinylether copolymer ethylene-tetrafluoride-based Teflon (Teflon PFA) , and PTFE/PFA composite Teflon. Moreover, though inferior to the above fluorocarbon polymer in corrosion resistance or weather resistance, silicone resin (particularly, thermosetting silicone resin) is also preferably used. Furthermore, it is possible to use epoxy resin or acrylic resin correspondingly to the purpose. Furthermore, it is preferable to form an insulating coating layer by using materials different from each other for a piezoelectric element and its vicinity and an electrode lead and its vicinity. Furthermore, it is preferable to add inorganic or organic filler to an insulating resin to adjust the rigidity of a diaphragm or the like.

When forming an insulating coating layer, one of various metals such as gold, silver, copper, nickel, and aluminum is preferably used as the material of a shielding layer formed on an insulating coating layer. Moreover, it is possible to use any one of the above-described metallic materials used for an electrode or the like of a piezoelectric element. Furthermore, it is possible to use conductive paste made by mixing metallic powder with resin.

Then, a device fabrication method of the present invention is described below by using the above device 31 as an example. Other devices 32 to 39 can be also fabricated by the same method. As described above, because a device is constituted with members including a fixing plate, it is possible to fabricate the device by connecting components made of various materials prepared as separate bodies. In this case, however, there is a problem on the reliability because the productivity is low and a joint is easily damaged. Therefore, in the case of the present invention, the green-sheet laminating method using ceramics powder as a material is preferably adopted.

Figure 11:
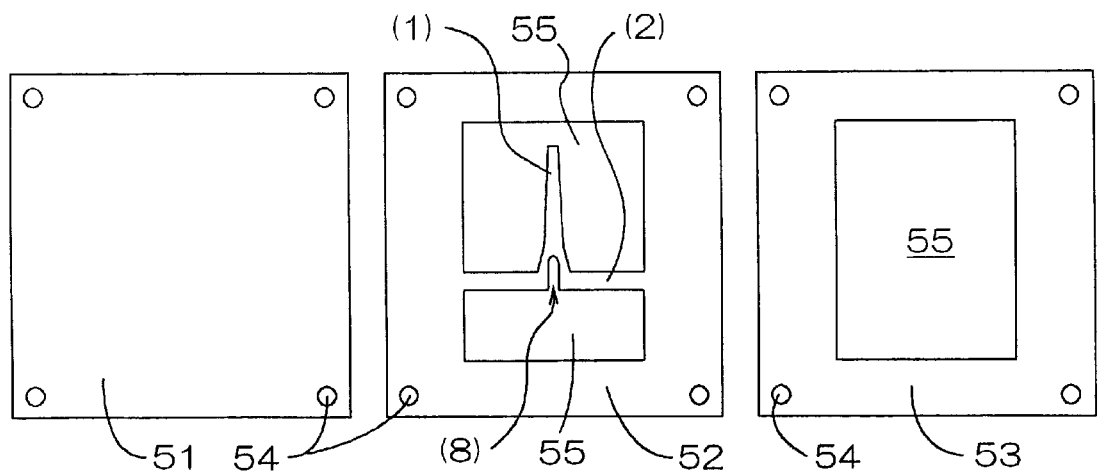
FIG. 11 shows a top view of a shape of a sheet member used to fabricate a piezoelectric/electrostrictive device of the present invention.

In the case of the green-sheet laminating method, slurry is first prepared by adding and mixing binder, solvent, and dispersant to ceramics powder such as zirconia and then slurry is degassed, and then form a green sheet or green tape having a predetermined thickness by the reverse roll coater method or doctor blade method or the like. Then, various green sheet members (hereafter referred to as "sheet members") shown in FIG. 11 are manufactured by punching the green sheet with a die.

A sheet member 51 is a member serving as a substrate 5, a connection plate 2, a fixing plate 1, and diaphragms 3A to 3D after firing or sintering the sheet member 51. At this point of time, however, the sheet member 51 is formed as a single plate in which those shapes are unclear. This is, as described above, because it is preferable to form the diaphragms 3A to 3D at a small thickness of 3 to 20 µm, and therefore, it is preferable to cut off unnecessary portions of the sheet member 51 through laser-beam processing after firing it compared to the case of forming the shapes of the above members on the sheet member 51 under a green sheet state because the shape accuracy is preferably maintained.

A sheet member 52 is a member serving as the substrate 5 and moreover for forming the fixing plate 1 and the connection plate 2 so that they become thicker than the diaphragms 3A to 3D, on which a hole 55, the fixing plate 1 and the connection plate 2 are formed. It is also possible to form a notch 8 at the joint between the fixed plate 1 and the connection plate 2. Desired thicknesses of the fixing plate 1 and the connection plate 2 are obtained by superimposing a predetermined number of sheet members 52 each other. To form the fixing plate 1 thinner than the connection plate 2, it is possible to manufacture sheet members respectively obtained by removing only a portion serving as the fixing plate 1 from the sheet member 52 and superimpose them on each other. The sheet member 53 with the hole 55 formed on it is a member serving as the substrate 5. By superimposing a predetermined number of sheet members, a desired thickness can be obtained.

A green layered product is manufactured by superimposing these sheet members 51 to 53 in order while positioning the members 51 to 53 by using a reference hole 54 and uniting them into one body by pressing under heating. Thereafter, the green layered product is sintered at a temperature of 1,200° C. to 1,600° C. It is preferable to previously form piezoelectric elements 4A to 4D at positions of the sheet member 51 on which the diaphragms 3A to 3D are finally formed and then, sinter them integrally with the green layered product. To arrange the piezoelectric elements 4A to 4D through co-firing, there is a method of forming piezoelectric films by the press forming method using a die or the tape forming method using slurry, thereby superimposing the piezoelectric films to be sintered on the sheet member 51 through pressing under applying heat to co-fire the piezoelectric films and the green layered product and simultaneously manufacturing a substrate and the piezoelectric films. In this case, however, it is necessary to previously form an electrodes on the substrate or piezoelectric films by a film-forming method to be mentioned later.

Though the temperature for sintering a piezoelectric film is properly determined depending on a material constituting the piezoelectric film, it is generally set to 800° C. to 1,400° C., preferably set to 1,000° C. to 1,400° C. In this case, to control the composition of the piezoelectric film, it is preferable to sinter the material of the piezoelectric film under the existence of the evaporation source of the material. Moreover, to sinter a piezoelectric film and a substrate at the same time, it is naturally necessary to match the firing condition of the piezoelectric film with that of the substrate.

Moreover, it is possible to arrange piezoelectric elements at the diaphragm-forming positions of a sintered layered product through one of the various thick-film-forming methods such as the screen printing method, dipping method, coating method, and electrophoresis or one of the various thin-film-forming methods such as the ion beam method, sputtering method, vacuum evaporation, ion plating method, chemical vapor deposition method (CVD), and plating. Among these methods, the present invention preferably adopts the thick-film-forming method according to one of the screen printing method, dipping method, and electrophoresis in order to form a piezoelectric film. This is because these methods make it possible to form a piezoelectric film by using paste, slurry, suspension, emulsion, or sol mainly containing piezoelectric ceramics particles having an average particle size of 0.01 to 5 µm, preferably 0.05 to 3 µm and obtain a preferable piezoelectric-operating characteristic. Moreover, particularly, the electrophoresis makes it possible to form a film at a high density and a high shape accuracy and has the characteristics described in the technical document "DENKI KAGAKU," 53, No. 1 (1985), pp. 63–68, written by K. Anzai." Therefore, it is preferable to properly select a method by considering a requested accuracy or reliability.

For example, it is possible to arrange piezoelectric elements after sintering a formed green layered product under a predetermined condition, then printing a first electrode at a predetermined position on the surface of a sintered sheet member 21 and firing or sintering it, then printing and sintering a piezoelectric film, and moreover printing and firing or sintering a second electrode. Then, an electrode lead for connecting an electrode of a piezoelectric element continuously formed to a measuring instrument is printed and fired. In this case, by using platinum (Pt) as the first electrode, lead zirconate titanate (PZT) as the piezoelectric film, and gold (Au) as the second electrode and moreover using silver (Ag) as the electrode lead, re-sintering of a material sintered before a certain sintering stage does not occur because the sintering or firing temperature in the sintering or firing process is set to be lower in order of layer formation, and it is possible to prevent trouble such as exfoliation or aggregation of electrode material or the like from occurring.

Moreover, by selecting a proper material, it is possible to successively print each member and electrode lead of a piezoelectric element and integrally sinter them at one time. On the other hand, it is possible to form a piezoelectric film and then, form each electrode at a low temperature. Furthermore, it is possible to form each member and electrode lead of a piezoelectric element through the thin-film method such as the sputtering method or vapor evaporation method. In this case, heat treatment is not always necessary.

Thus, by forming a piezoelectric element through a film-forming method, it is possible to integrally bond and arrange a piezoelectric element and a diaphragm without using an adhesive, secure the reliability and reproducibility, and simplify integration. In this case, it is also possible to form a proper pattern on a piezoelectric film. To form the pattern, it is possible to use the screen printing method, photolithography method, or laser-beam machining method, or a machining method such as the slicing method or ultrasonic machining method.

Then, the diaphragms 3A to 3D, fixing plate 1, and connection plate 2 or the notch 8 if necessary are formed at predetermined positions of a sintered layered product on which the piezoelectric elements 4A to 4D and electrode leads are formed. In this case, it is preferable to cut out, machine, and remove unnecessary portions from the sintered sheet member 21 through the machining using the fourth harmonic wave of a YAG laser. Thus, it is possible to machine the diaphragms 3A to 3D, fixing plate 1, and connection plate 2 into the shapes shown in FIG. 1. It is also possible to remove an unnecessary portion corresponding to the substrate 5 through the laser-beam machining or dicing. Moreover, it is preferable to adjust a displacement amount by adjusting the shapes of the fixing plate 1 and connection plate 2 mainly formed with the sheet member 22 or the shapes of the diaphragms 3A to 3D formed with the sheet member 21 under such a processing.

Figure 15:
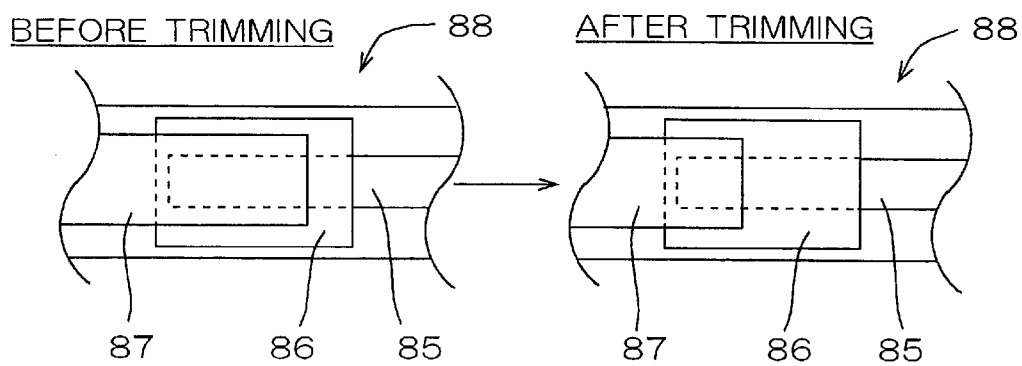
FIG. 15 shows an explanatory view of an example of a method for finishing a piezoelectric element of a piezoelectric/electrostrictive device of the present invention.
Figure 16:
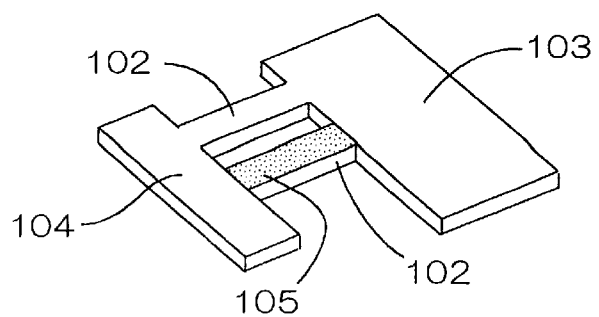
FIG. 16 shows an example of a perspective view of the structure of a conventional piezoelectric/electrostrictive device (piezoelectric actuator).

Furthermore, it is preferable to obtain a predetermined displacing characteristic by setting the piezoelectric element 88 shown in FIG. 12 in which the second electrode 87 is used as an upper electrode and the first electrode 85 as a lower electrode and the piezoelectric film 86 is formed between the upper and lower electrodes as shown in FIG. 15 and thereafter, removing the upper electrode through the YAG fourth harmonic laser beam or mechanical machining and adjusting the available electrode area of the piezoelectric element 88 to adjust the electrical characteristic such as the impedance of a piezoelectric/electrostrictive device. When the piezoelectric element 88 has the comb-shaped structure shown in FIG. 13 or 14, it is necessary to remove a part of one or both electrodes.

For the above machining, it is possible to use one of such machining methods suitable for the size and shape of a driving or movable portion as the laser-beam machining using a YAG laser beam, second or third harmonic wave, excimer laser beam, or $CO_2$ laser beam, electron-beam machining, and dicing (machining), in addition to the machining using the above YAG fourth harmonic laser beam.

Moreover, it is possible to fabricate a device of the present invention by using one of the pressure forming method using a forming die, casting method, and injection molding method in addition to the above fabrication method using a green sheet. In this case, machining such as cutting, grinding, laser-beam machining, punching using a punch, or ultrasonic machining is applied to the device before and after sintering it and the device is formed into a predetermined shape.

An insulating coating layer formed on the piezoelectric elements 4A to 4D and a electrode lead of the device 31 thus fabricated can be formed through the screen printing method, coating method, or spraying method by using glass or resin. In this case, when using glass as a material, it is necessary to raise the temperature of the device up to approx. the softening point of the glass, and it is preferable to use resin because the resin is soft and requires only drying or curing at low temperature though a displacement or vibration may be decreased because the glass has a high hardness.

It is already described that either of fluorocarbon polymer and silicone resin is preferably used as the resin for an insulating coating layer. However, when using either of these resins, it is preferable to form a primer layer corresponding to the types of the resin used and ceramics serving as a substrate and form an insulating coating layer on the primer layer in order to improve the adhesiveness between the ceramics and insulating coating layer.

Then, a shielding layer to be formed on an insulating coating layer is formed through a method not requiring heating such as the sputtering method when using various metals because it is difficult to perform heat-treatment or firing if the insulating coating layer is made of resin. However, when using conductive paste made of metallic powder and resin, it is possible to preferably use the screen printing method or coating method. Moreover, when forming the insulating coating layer with glass, it is possible to screen-print the conductor paste and then fired it at a temperature lower than that of flowing of glass.

Modes, materials, and fabrication methods of a piezoelectric/electrostrictive device of the present invention are described above in detail. However, it is needless to say that the present invention is not restricted to the above embodiments. The present invention allows a modified, corrected, or improved embodiment in accordance with the knowledge of a person of ordinary skill in the art as long as the embodiment is not deviated from the gist of the present invention, in addition to the above embodiments.

As described above, a piezoelectric/electrostrictive device of the present invention has features that the structure is simple and the device can be easily decreased in size and weight and it is not easily influenced by external harmful vibrations. Moreover, the device has features that accurate control is realized for both static displacement and dynamic displacement and a large amount of displacement can be easily obtained and moreover, when using the device as a sensor, the sensitivity can be raised. Furthermore, by using a simple fabrication method such as the green-sheet laminating method, an advantage is obtained that the device can be inexpensively fabricated while improving the reliability as an integral structure. Furthermore, an advantage is obtained that the allowable range for selecting a component material is wide and a preferable material can be used correspondingly to the purpose at any time. Therefore, when setting the device into various actuators and sensors, it realizes high-accuracy control and measurement and the device shows a superior advantage that it contributes to the decrease in size and weight.

What is claimed is:

1. A piezoelectric/electrostrictive device comprising:
   a substrate having two pairs of concave recesses formed therein, the bottom of each recess defining a diaphragm extending in a first longitudinal direction;
   a connection plate having a first end secured between two of said diaphragms and an opposed second end secured between the other two diaphragms, said connection plate extending in a direction substantially perpendicular to said first longitudinal direction and being spanned between and connected to the bottoms of said pairs of concave recesses;
   piezoelectric/electrostrictive elements arranged on at least a part of a planar surface of each diaphragm; and
   a fixing plate connected to the connection plate and extending in a longitudinal direction substantially parallel to said first longitudinal direction.

2. The piezoelectric/electrostrictive device according to claim 1, wherein a notch is formed at a joint between the fixing plate and the connection plate.

3. The piezoelectric/electrostrictive device according to claim 1, wherein the connection plate is divided into two plates in the spanning direction of the connection plate, and a gap is formed at the central portion of the connection plate, and the fixing plate is connected to a planar surface of the connection plate so as to cross the gap.

4. The piezoelectric/electrostrictive device according to claim 3, wherein a notch is formed at an end of the fixing plate at a position for crossing the divided connection plates.

5. The piezoelectric/electrostrictive device according to claim 1, wherein the fixing plate is connected so as to intersect the connection plate.

6. The piezoelectric/electrostrictive device according to claim 1, wherein a notch is formed in the connection plate between the joint between the connection plate and the substrate and the joint between the connection plate and the diaphragm.

7. The piezoelectric/electrostrictive device according to claim 1, wherein the connection plate is divided into at least two plates in the longitudinal direction of the fixing plate and the fixing plate is connected with at least two divided and formed connection plates.

8. The piezoelectric/electrostrictive device according to claim 2, wherein a hinge portion is provided for the fixing plate from the joint between the fixing plate and the connection plate in the longitudinal direction of the fixing plate.

9. The piezoelectric/electrostrictive device according to claim 1, wherein a set of piezoelectric elements located at diagonal positions are driven at the same phase and another set of piezoelectric elements are driven at the opposite phase centering around a joint between the fixing plate and the connection plate.

10. The piezoelectric/electrostrictive device according to claim 6, wherein a set of piezoelectric elements at line-symmetric positions are driven at the same phase and another set of piezoelectric elements are driven at the opposite phase by using the longitudinal axis of the fixing plate as a symmetric axis.

11. The piezoelectric/electrostrictive device according to claim 1, wherein a pair of diaphragms for holding the connection plate is connected with the connection plate at positions shifted in the thickness direction of the connection plate.

12. The piezoelectric/electrostrictive device according to claim 11, wherein the piezoelectric elements are arranged on planar surface of each of the diaphragms by using a middle point between the connection positions of a pair of diaphragms for holding the connection plate with the connection plate as a point-symmetry center and the piezoelectric elements are driven at the same phase.

13. A piezoelectric/electrostrictive device comprising:
   a substrate having a concave recess formed therein, said recess being defined by at least two opposed sides and a third side between said two opposed sides;
   a connection plate spanned between opposed sides of said concave recess;
   at least two diaphragms, on which piezoelectric/electrostrictive elements are arranged on at least a part of at least one planar surface thereof, said diaphragms being spanned between the connection plate and the third side of said concave recess; and
   a fixing plate connected to the connection plate, the longitudinal direction of the fixing plate being substantially parallel with the spanning direction of the diaphragms.

14. The piezoelectric/electrostrictive device according to claim 13, wherein at least two pairs of diaphragms constituted so as to face a plane surface are spanned between the connection plate and the bottom of the concave portion of the substrate.

15. The piezoelectric/electrostrictive device according to claim 13, wherein a notch is formed at a joint between the fixing plate and the connection plate.

16. The piezoelectric/electrostrictive device according to claim 13, wherein the connection plate is divided into two plates in the spanning direction of the connection plate, a gap is formed at the central portion of the connection plate, and the fixing plate is connected to the planar surface of the connection plate so as to cross the gap.

17. The piezoelectric/electrostrictive device according to claim 16, wherein a notch is formed at an end of the fixing plate at a position crossing the divided connection plates.

18. The piezoelectric/electrostrictive device according to claim 1, wherein every connection of two optional members selected from the connection plate, the diaphragms, and the substrate is made at each side.

19. The piezoelectric/electrostrictive device according to claim 13, wherein every connection of two optional members selected from the connection plate, the diaphragms, and the substrate is made at each side.

20. The piezoelectric/electrostrictive device according to claim 1, wherein at least the connection plate, the diaphragms, and the substrate are integrally formed.

21. The piezoelectric/electrostrictive device according to claim 13, wherein at least the connection plate, the diaphragms, and the substrate are integrally formed.

22. The piezoelectric/electrostrictive device according to claim 1, wherein at least each portion of a device excluding the piezoelectric element is formed by a green-sheet laminating method.

23. The piezoelectric/electrostrictive device according to claim 13, wherein at least each portion of a device excluding the piezoelectric element is formed by a green-sheet laminating method.

24. The piezoelectric/electrostrictive device according to claim 1, wherein the displacing mode of the fixing plate uses at least any one of the displacement of uniaxial mode of the fixing plate in its longitudinal direction, displacement of in-plane rotation mode about the vicinity of a joint between the fixing plate and the connection plate, and displacement of rotation mode about the longitudinal axis of the connection plate.

25. The piezoelectric/electrostrictive device according to claim 24, wherein the displacement of in-plane rotation mode is based on a magnification mechanism for magnifying a displacement of the piezoelectric element in two steps.

26. The piezoelectric/electrostrictive device according to claim 13, wherein the displacing mode of the fixing plate uses at least any one of the displacement of uniaxial mode of the fixing plate in its longitudinal direction, displacement of in-plane rotation mode about the vicinity of a joint between the fixing plate and the connection plate, and displacement of rotation mode about the longitudinal axis of the connection plate.

27. The piezoelectric/electrostrictive device according to claim 26, wherein the displacement of in-plane rotation mode is based on a magnification mechanism for magnifying the displacement of the piezoelectric element in two steps.

28. The piezoelectric/electrostrictive device according to claim 1, wherein one piezoelectric element is divided into two elements, one of the divided piezoelectric elements is used as a driving element and the other of the divided piezoelectric element is used as an auxiliary element.

29. The piezoelectric/electrostrictive device according to claim 13, wherein one piezoelectric element is divided into two elements, one of the divided piezoelectric elements is used as a driving element and the other of the divided piezoelectric element is used as an auxiliary element.

30. The piezoelectric/electrostrictive device according to claim 1, wherein the piezoelectric element and an electrode lead electrically connected with the piezoelectric element are covered with an insulating coating layer made of resin or glass.

31. The piezoelectric/electrostrictive device according to claim 30, wherein the resin includes fluorocarbon polymer or silicone resin.

32. The piezoelectric/electrostrictive device according to claim 30, wherein a shielding layer made of a conductive member is further formed on the surface of the insulating coating layer.

33. The piezoelectric/electrostrictive device according to claim 13, wherein the piezoelectric element and an electrode lead electrically connected with the piezoelectric element are covered with an insulating coating layer made of resin or glass.

34. The piezoelectric/electrostrictive device according to claim 33, wherein the resin includes fluorocarbon polymer or silicone resin.

35. The piezoelectric/electrostrictive device according to claim 33, wherein a shielding layer made of a conductive member is further formed on the surface of the insulating coating layer.

36. The piezoelectric/electrostrictive device according to claim 1, wherein the substrate, the fixing plate, the connection plate, and the diaphragms are made of fully stabilized zirconia or partially stabilized zirconia.

37. The piezoelectric/electrostrictive device according to claim 13, wherein the substrate, the fixing plate, the connection plate, and the diaphragms are made of fully stabilized zirconia or partially stabilized zirconia.

38. The piezoelectric/electrostrictive device according to claim 1, wherein a piezoelectric film of the piezoelectric element consists essentially of lead zirconate, lead titanate, and lead magnesium niobate as major component.

39. The piezoelectric/electrostrictive device according to claim 13, wherein a piezoelectric film of the piezoelectric element consists essentially of lead zirconate, lead titanate, and lead magnesium niobate as major component.

40. The piezoelectric/electrostrictive device according to claim 1, wherein the shape of any one of the fixing plate, the connection plate, and the diaphragms is dimension-adjusted by trimming it through laser-beam machining or mechanical machining.

41. The piezoelectric/electrostrictive device according to claim 13, wherein the shape of any one of the fixing plate, the connection plate, and the diaphragms is dimension-adjusted by trimming it through laser-beam machining or mechanical machining.

42. The piezoelectric/electrostrictive device according to claim 1, wherein the available electrode area of the piezoelectric element is adjusted by laser-beam machining or mechanical machining.

43. The piezoelectric/electrostrictive device according to claim 13, wherein the available electrode area of the piezoelectric element is adjusted by laser-beam machining or mechanical machining.

44. The piezoelectric/electrostrictive device according to claim 1, wherein the piezoelectric/electrostrictive device is constituted with two or more piezoelectric/electrostrictive devices in which at least their fixing plates are connected with each other.

45. The piezoelectric/electrostrictive device according to claim 13, wherein the piezoelectric/electrostrictive device is constituted with two or more piezoelectric/electrostrictive devices in which at least their fixing plates are connected with each other.

* * * * *